(12) United States Patent
Salvemini et al.

(10) Patent No.: US 11,708,346 B2
(45) Date of Patent: Jul. 25, 2023

(54) TREATMENT AND PREVENTION OF NEUROPATHIC PAIN WITH P2Y14 ANTAGONISTS

(71) Applicants: Saint Louis University, St. Louis, MO (US); The United States of America, as represented by the Secretary, Department of Health and Human Service, Bethesda, MD (US)

(72) Inventors: Daniela Salvemini, Chesterfield, MO (US); Kenneth Alan Jacobson, Silver Spring, MD (US)

(73) Assignee: Saint Louis University, St. Louis, MO (US)

( * ) Notice: Subject to any disclaimer, the term of this patent is extended or adjusted under 35 U.S.C. 154(b) by 126 days.

(21) Appl. No.: 16/936,951

(22) Filed: Jul. 23, 2020

(65) Prior Publication Data

US 2021/0024489 A1 Jan. 28, 2021

Related U.S. Application Data

(60) Provisional application No. 63/013,792, filed on Apr. 22, 2020, provisional application No. 62/877,385, filed on Jul. 23, 2019.

(51) Int. Cl.
| | | |
|---|---|---|
| *C07D 401/10* | (2006.01) | |
| *A61P 25/02* | (2006.01) | |
| *A61K 31/4192* | (2006.01) | |
| *A61K 31/454* | (2006.01) | |
| *C07D 211/34* | (2006.01) | |
| *C07K 16/28* | (2006.01) | |

(52) U.S. Cl.
CPC ........ *C07D 401/10* (2013.01); *A61K 31/4192* (2013.01); *A61K 31/454* (2013.01); *A61P 25/02* (2018.01); *C07D 211/34* (2013.01); *C07K 16/28* (2013.01)

(58) Field of Classification Search
CPC ... C07D 401/10; A61P 25/02; A61K 31/4192; A61K 31/454
See application file for complete search history.

(56) References Cited

U.S. PATENT DOCUMENTS

| 10,683,277 B2 | 6/2020 | Jacobson et al. |
| 2017/0312247 A1 | 11/2017 | Liu et al. |
| 2018/0297981 A1 | 10/2018 | Jacobson et al. |

FOREIGN PATENT DOCUMENTS

| WO | WO-2007020935 A1 * | 2/2007 | ......... A61K 31/4152 |
| WO | 2015070001 A2 | 5/2015 | |
| WO | 2019157417 A1 | 8/2019 | |

OTHER PUBLICATIONS

Kobayashi et al., Glia, 2012, 60(10), pp. 1529-1539. (Year: 2012).*
An English machine translation of WO 2007/020935 A1, 2007. (Year: 2007).*
Chambers et al., A G Protein-coupled Receptor for UDP-glucose*; The Journal of Biological Chemistry; 2000, vol. 275, No. 15, pp. 10767-10771.
Chaplan et al., Quantitative assessment of tactile allodynia in the rat paw; Journal of Neuroscience Methods vol. 53, Issue 1, Jul. 1994, pp. 55-63.
Yu et al., Structure-Guided Modification of Heterocyclic Antagonists of the P2Y14 Receptor; J Med Chem., 2018, vol. 61, No. 11, pp. 4860-4882.

* cited by examiner

*Primary Examiner* — Laura L Stockton
(74) *Attorney, Agent, or Firm* — Stinson LLP

(57) ABSTRACT

Disclosed herein are methods for treating neuropathic pain in a subject in need thereof. The methods include: administering to a subject in need thereof a therapeutically effective amount of an antagonist of P2Y14.

2 Claims, 14 Drawing Sheets

(20)

TREATMENT AND PREVENTION OF NEUROPATHIC PAIN WITH P2Y14 ANTAGONISTS

CROSS-REFERENCE TO RELATED APPLICATIONS

This application claims priority to U.S. Provisional Patent Application Ser. No. 62/877,385, filed on Jul. 23, 2019 and U.S. Provisional Patent Application Ser. No. 63/013,792, filed Apr. 22, 2020, the disclosure of each of which is hereby incorporated by reference in its entirety.

BACKGROUND OF THE DISCLOSURE

The present disclosure generally relates to medicine. More particularly, the present disclosure is directed to methods for preventing and treating neuropathic pain using selective antagonists for the P2Y14 receptor. The P2Y14 receptor is a G protein-coupled receptor that is activated by extracellular UDP-glucose and related nucleotides, which act as DAMPs (damage-associated molecular patterns).

Pain is an unpleasant feeling often caused by intense or damaging stimuli. The International Association for the Study of Pain's widely used definition states: "Pain is an unpleasant sensory and emotional experience associated with actual or potential tissue damage, or described in terms of such damage." Pain motivates the individual to withdraw from damaging situations, to protect a damaged body part while it heals, and to avoid similar experiences in the future. Most pain resolves promptly once the painful stimulus is removed and the body has healed, but sometimes pain persists despite removal of the stimulus and apparent healing of the body; and sometimes pain arises in the absence of any detectable stimulus, damage or disease.

Pain is the most common reason for physician consultation in the United States. It is a major symptom in many medical conditions, and can significantly interfere with a person's quality of life and general functioning. Psychological factors such as social support, hypnotic suggestion, excitement, or distraction can significantly modulate pain's intensity or unpleasantness.

The International Association for the Study of Pain (IASP) has classified pain according to specific characteristics: (a) region of the body involved (e.g., abdomen, lower limbs), (b) system whose dysfunction may be causing the pain (e.g., nervous, gastrointestinal), (c) duration and pattern of occurrence, (d) intensity and time since onset, and (e) etiology. This system has been criticized by Clifford J. Woolf and others as inadequate for guiding research and treatment. According to Woolf, there are three classes of pain: nociceptive pain (see hereunder), inflammatory pain which is associated with tissue damage and the infiltration of immune cells, and pathological pain which is a disease state caused by damage to the nervous system (neuropathic pain, see hereunder) or by its abnormal function (dysfunctional pain, like in fibromyalgia, irritable bowel syndrome, tension type headache, etc.).

Neuropathic pain conditions arising from injuries to the nervous system due to trauma, disease or neurotoxins are exceedingly difficult to treat. Clinicians and patients are often left to manage neuropathic pain with opioids, but these approaches are limited by the eventual loss in opioid efficacy with developing antinociceptive tolerance, the occurrence of severe adverse side effects with prolonged opioid use and the strong potential for their abuse. With over 15-20 million people in the US affected by neuropathic pain, a high priority has been placed upon developing novel non-narcotic analgesics.

Accordingly, there exists a need to develop methods for treating neuropathic pain.

BRIEF DESCRIPTION OF THE DISCLOSURE

The present disclosure is generally related to methods for treating neuropathic pain. More particularly, the present disclosure is directed to methods for treating neuropathic pain using P2Y14 receptor antagonists. Additionally, the present disclosure is directed to compounds that function as P2Y14 antagonists and can be administered for treating neuropathic pain.

In one aspect, the present disclosure is directed to a method for treating neuropathic pain. The method includes: administering to a subject in need thereof a P2Y14 antagonist. Particularly suitable P2Y14 antagonists have a naphthalene or phenyl-triazolyl scaffold.

In another aspect, the present disclosure is directed to a compound having the formula selected from the group consisting of:

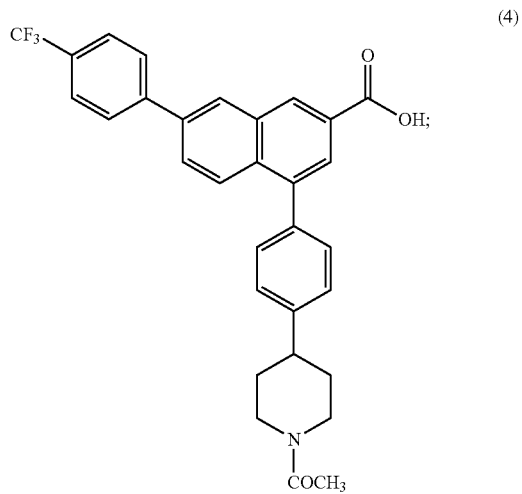

(4)

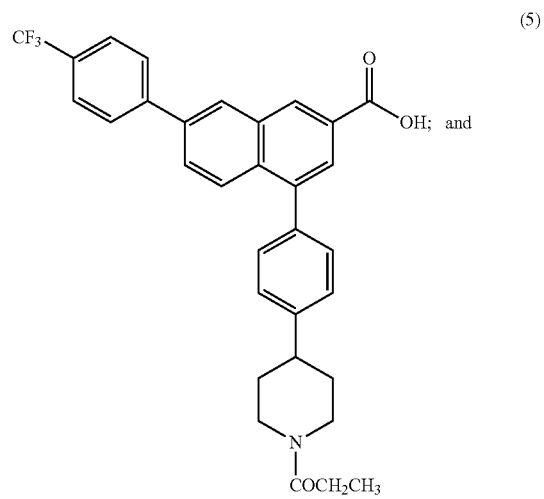

(5)

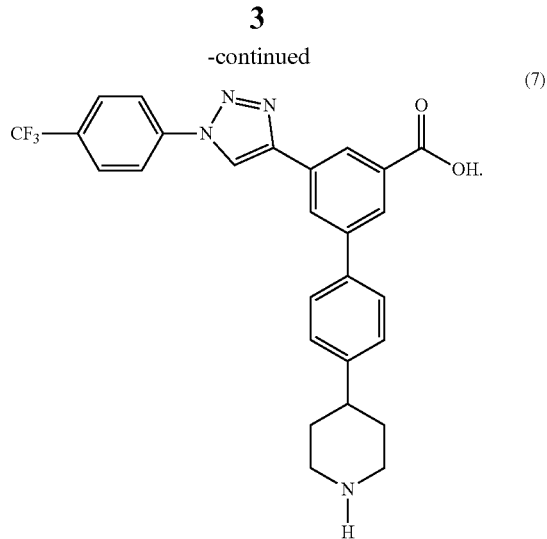

(7)

BRIEF DESCRIPTION OF THE DRAWINGS

The disclosure will be better understood, and features, aspects and advantages other than those set forth above will become apparent wen consideration is given to the following detailed description thereof. Such detailed description makes reference to the following drawings, wherein:

FIG. 1B depicts untreated cells. FIG. 1C depicts cells incubated for 30 min with 200 nM 20 alone. FIG. 1D depicts cells incubated for 30 min with 1 M 1 followed by 30 min with 200 nM 20.

DETAILED DESCRIPTION

Figure 1A:
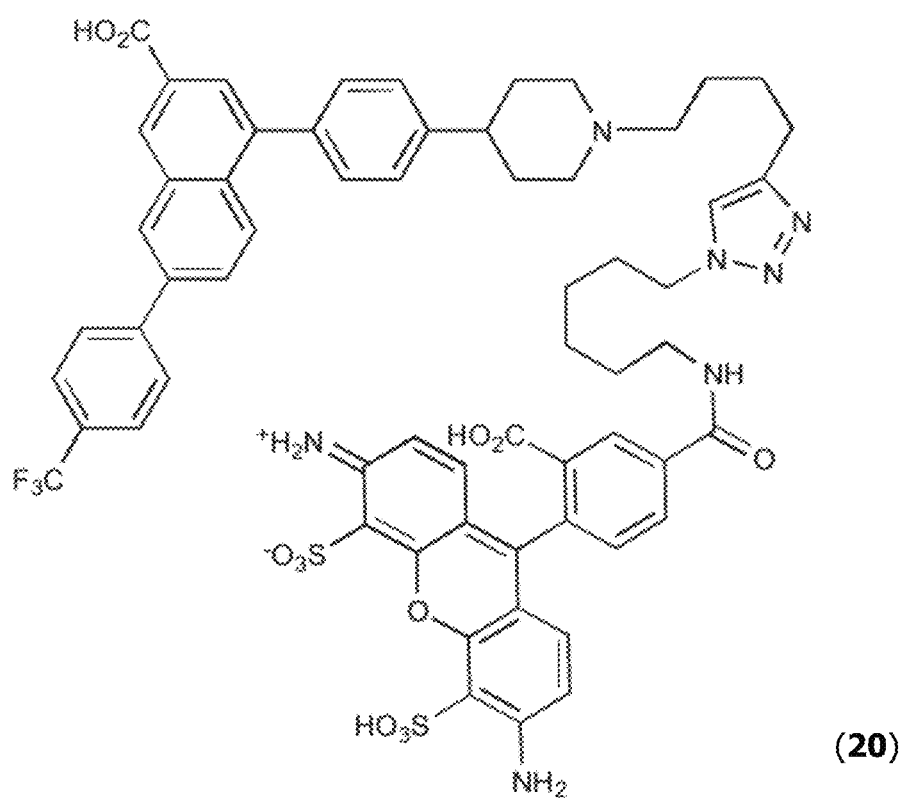
FIG. 1A depicts the structure of compound (20), a high affinity fluorescent tracer antagonists for $P2Y_{14}R$ binding assays. The fluorophore is AlexaFluor488, and the pharmacophore is an N-alkyl derivative of compound 1.
Figure 1B:
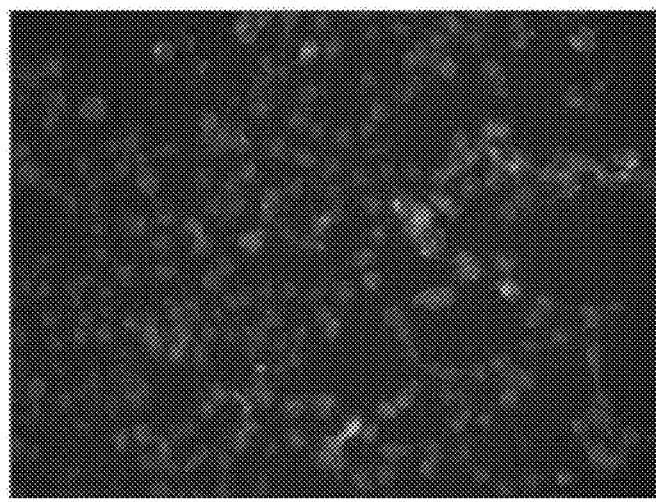
FIGS. 1B-1D depicts fluorescence micrographs of $mP2Y_{14}R$-expressing HEK293 cells.
Figure 1C:
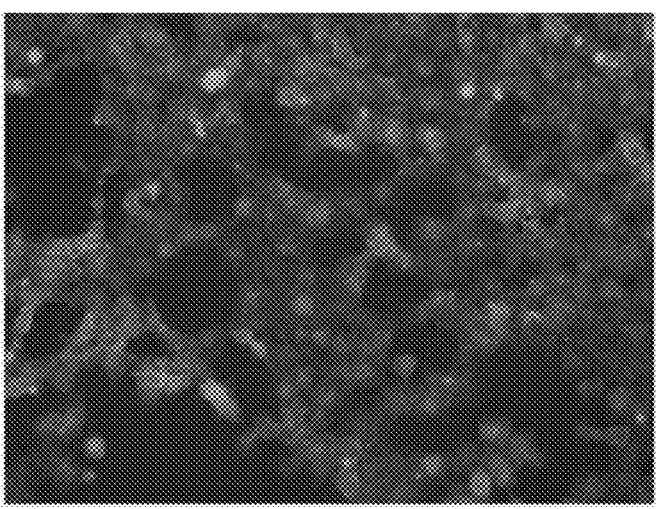
Figure 1D:
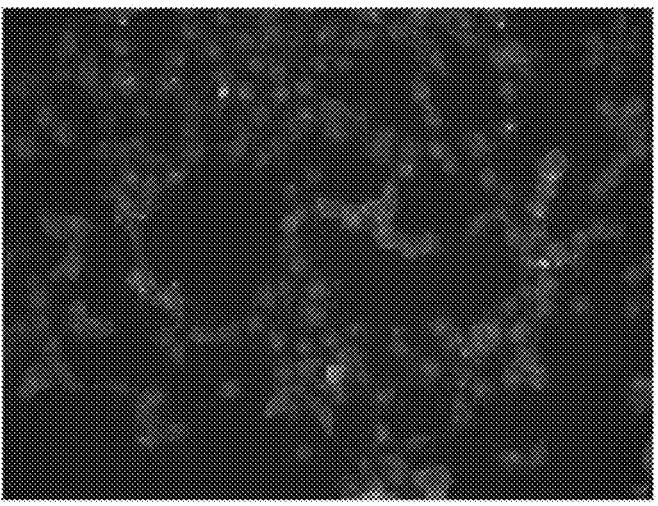
Figure 2A:
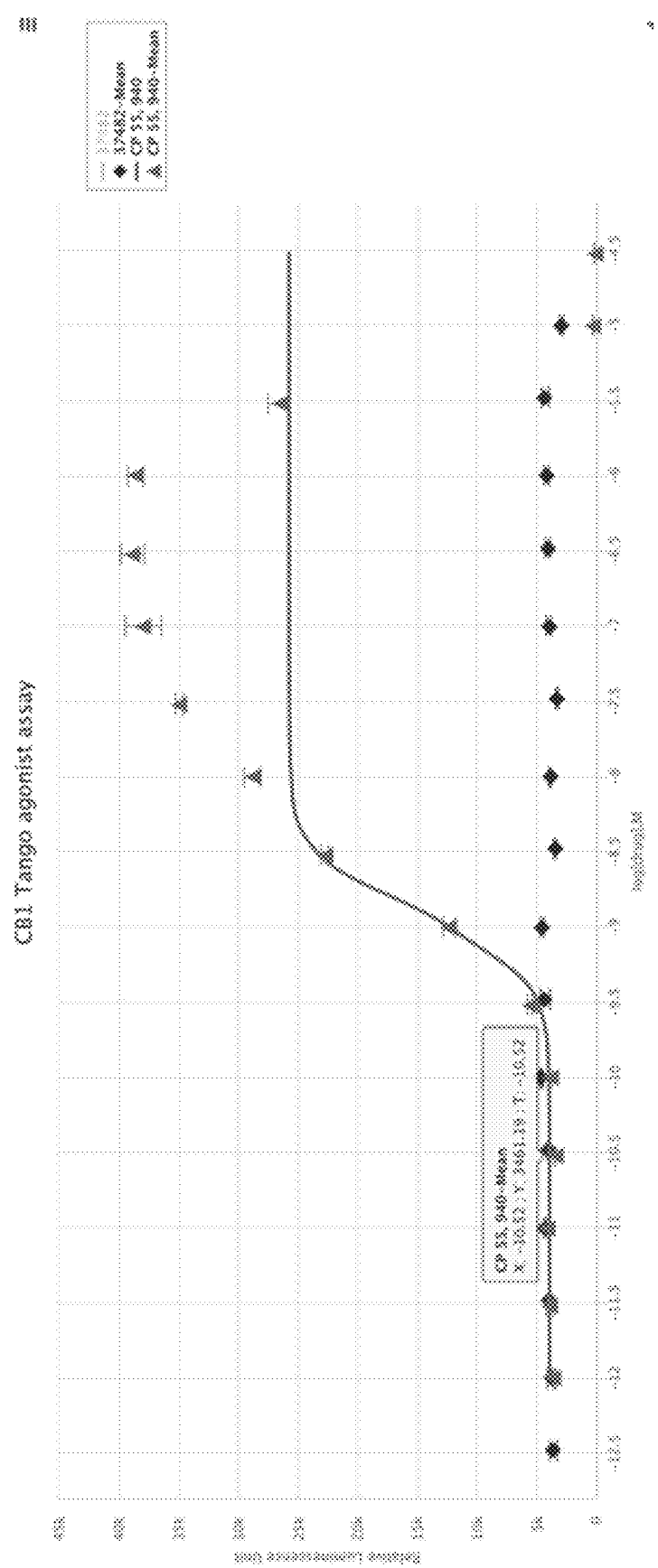
FIGS. 2A & 2B depict results of CB1 agonist and antagonist assays of compound 1.
Figure 2B:
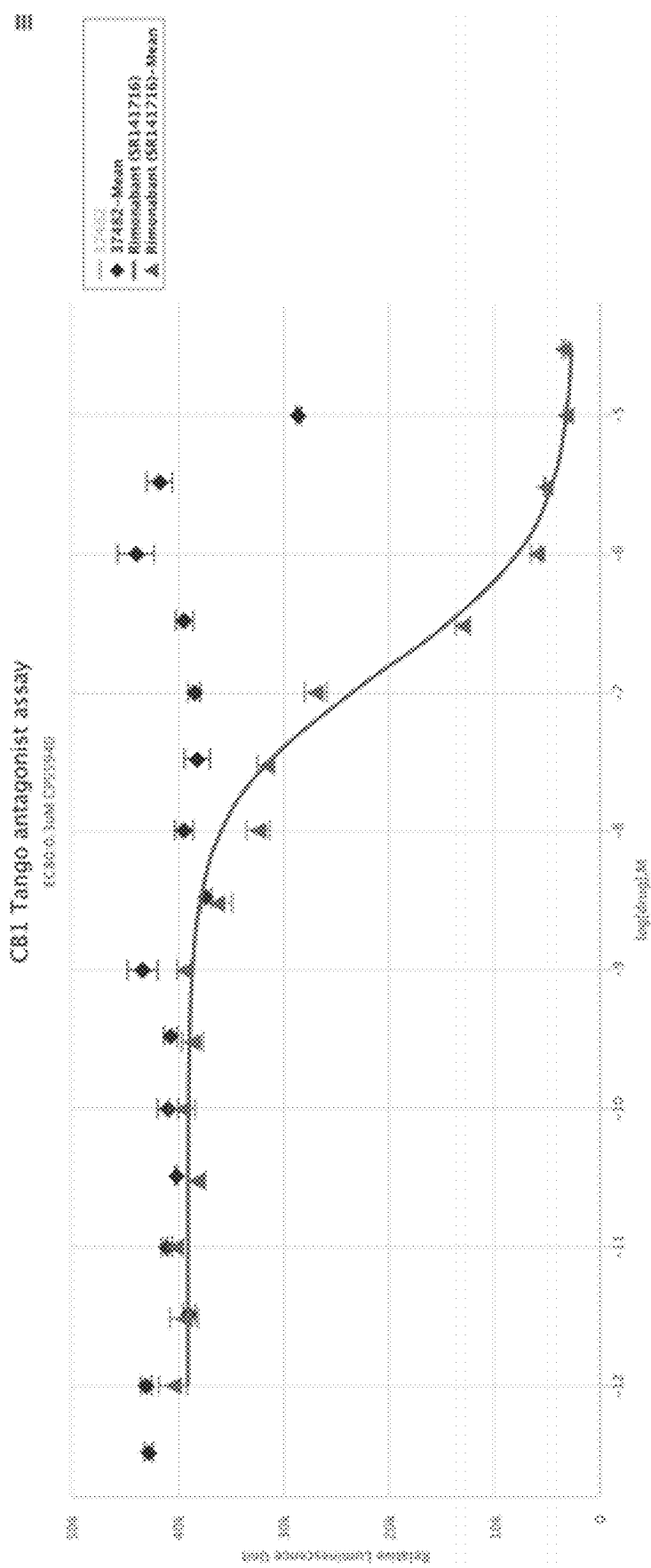
Figure 2C:
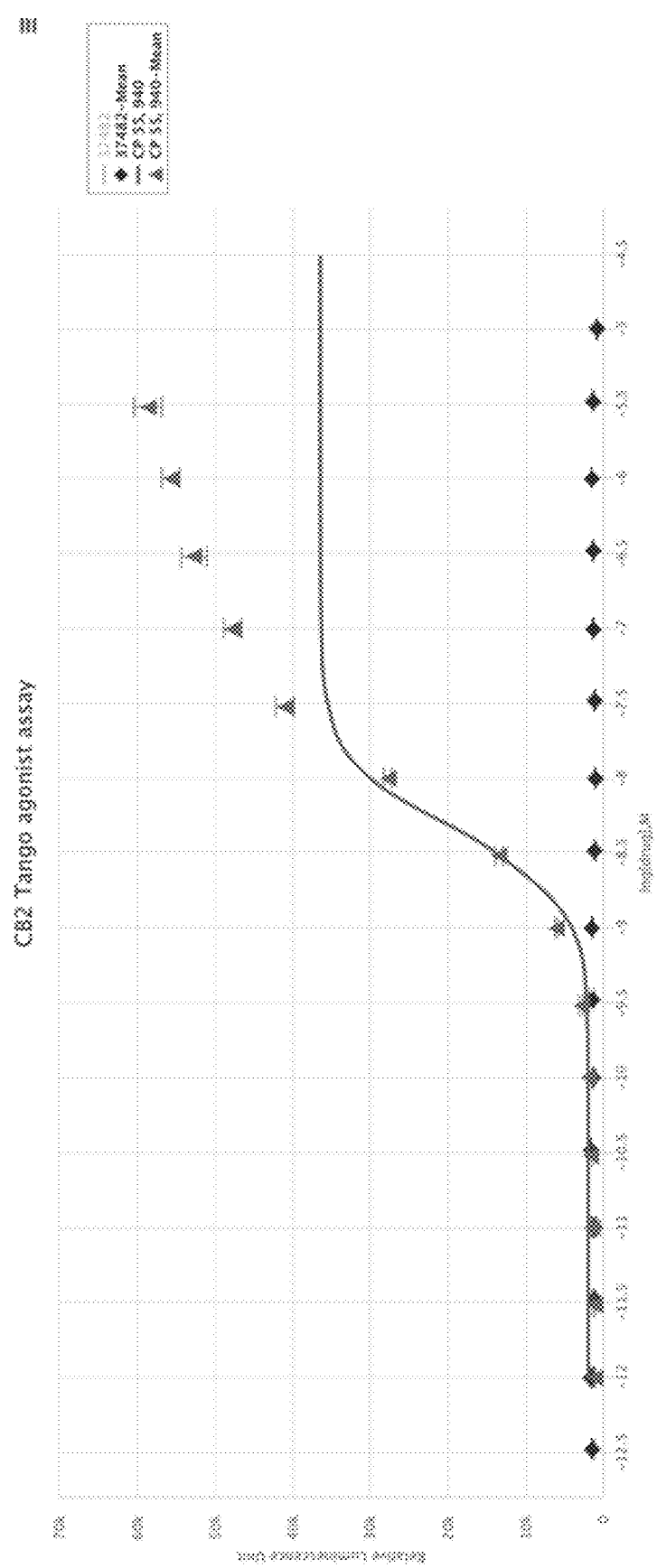
FIGS. 2C & 2D depict results of CB2 agonist and antagonist assays of compound 1.
Figure 2D:
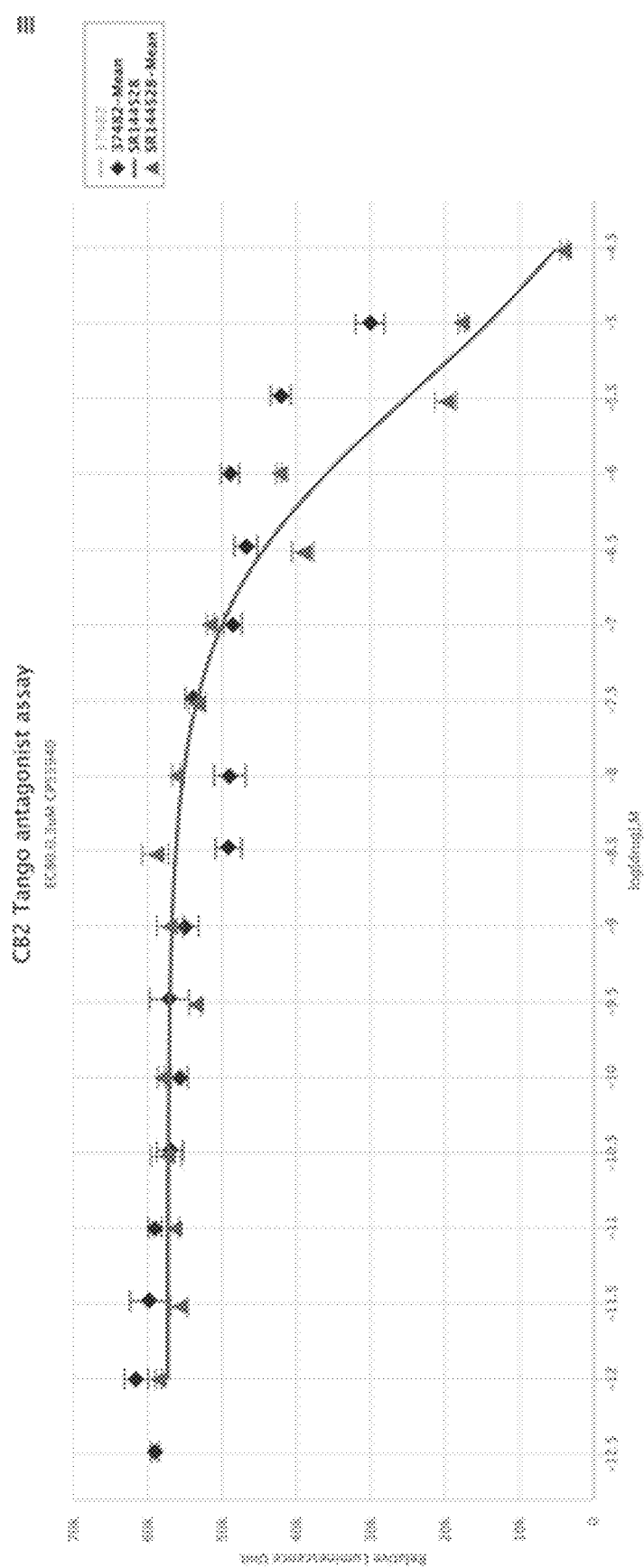
Figure 3A:
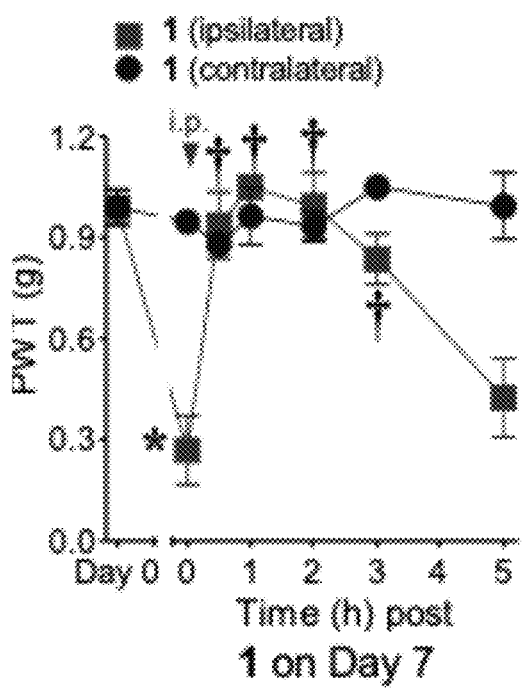
FIGS. 3A-3C depict representative time plots of the effects of $P2Y_{14}R$ antagonists to alleviate CCI-induced neuropathic pain in adult male ICR mice, 7 days post-CCI of the sciatic nerve. Mechano-allodynia in the ipsilateral hind paw was measured with manual von Frey filaments, according to the up and down method, and compared to the contralateral side. A single injection (10 µmol/kg, i.p.) of a $P2Y_{14}R$ antagonist (compounds 1, 2, 4 and 7) reversed the allodynia. Results are presented as mean±SD. Data was analyzed by two-way ANOVA, *P<0.05 vs. Day 0 and †P<0.05 vs. Day 7. Mean±SD, n=3. Vehicle was 30% DMSO in phosphate-buffered saline, in a volume of 0.2 mL.
Figure 3B:
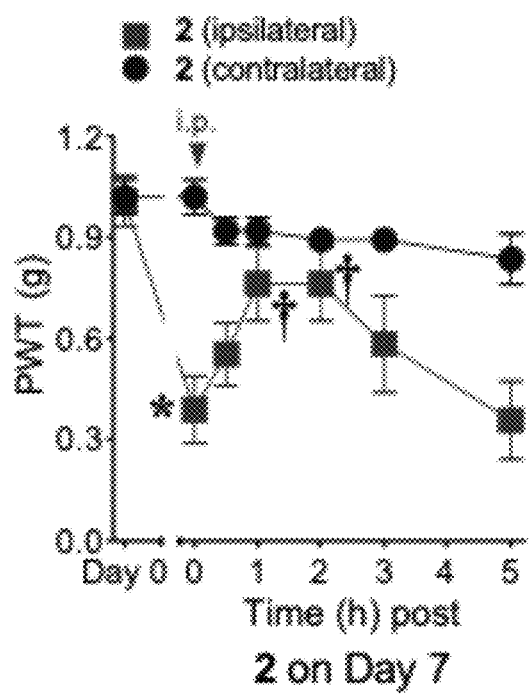
Figure 3C:
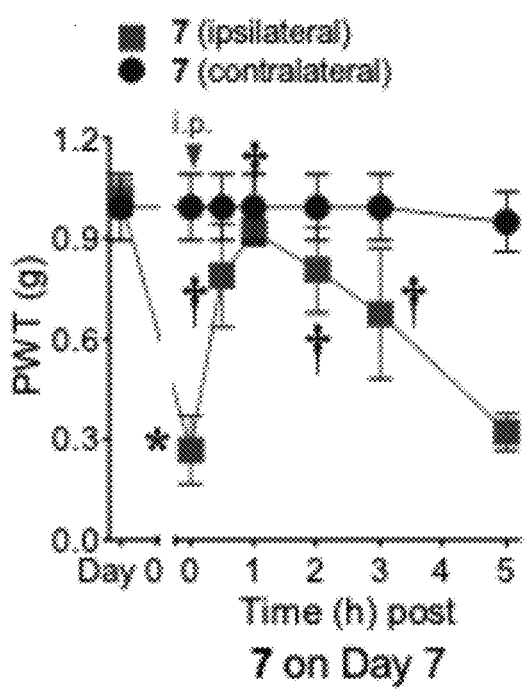
Figure 3D:
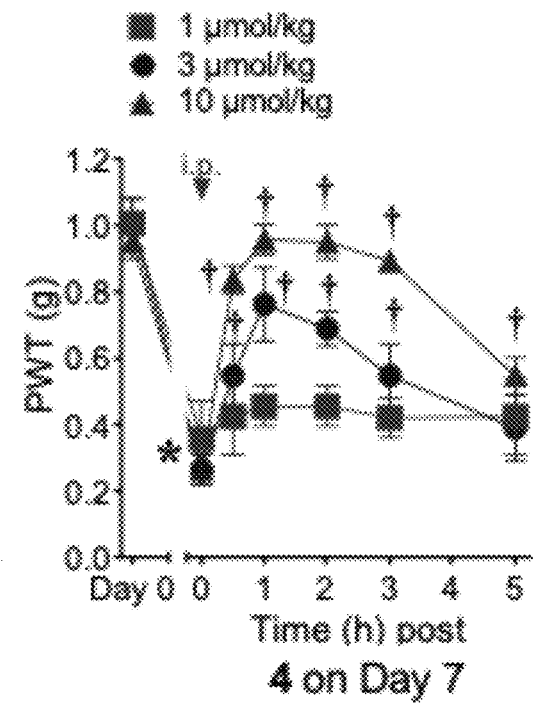
FIG. 3D depicts representative dose dependent plots of the effects of the $P2Y_{14}R$ antagonists analyzed in FIGS. 2A-2C.
Figure 4A:
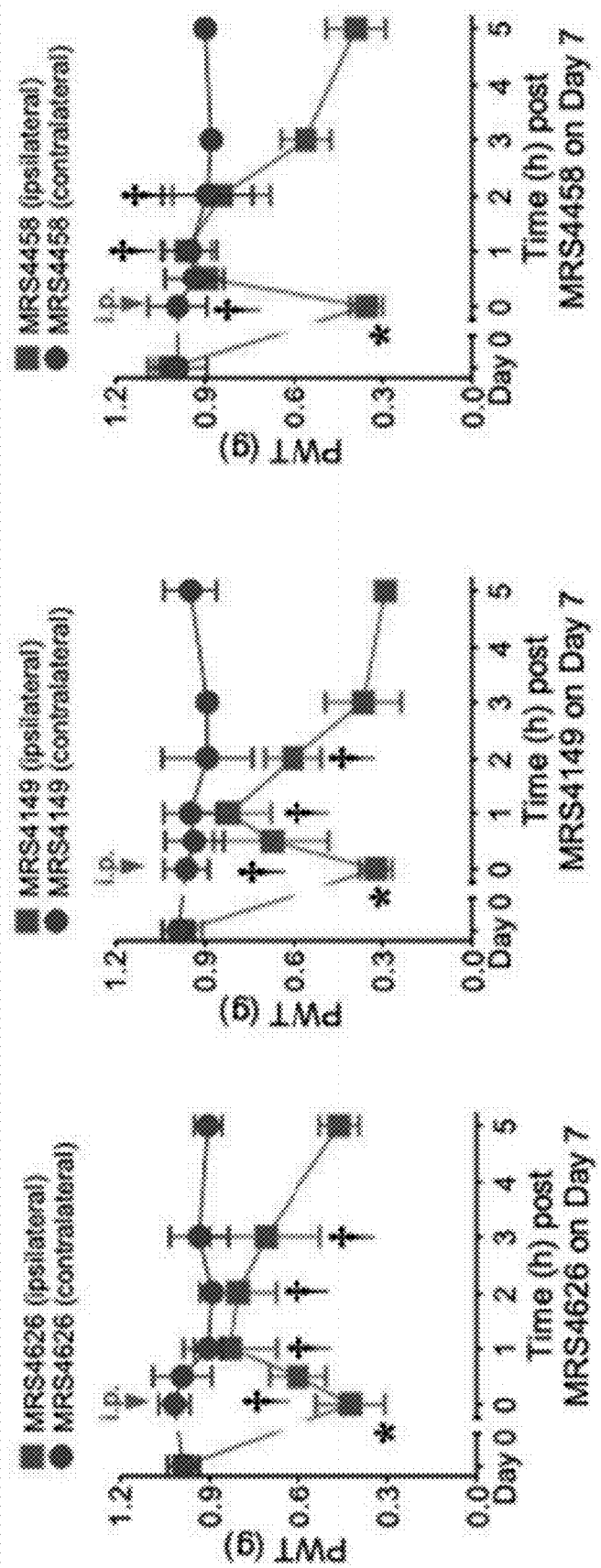
FIGS. 4A-4F depict representative time plots of reversal by P2Y14R antagonists of CCI-induced mechano-allodynia in mice (10 µmol/kg, unless noted). Injection vehicle (i.p.) is 5% DMSO in water (0.2 mL). Mean±SD, n=3, ANOVA, *P<0.05 vs. Day 0 and †P<0.05 vs. Day 7. Key: 1, MRSPPTN: 2, MRS4519; 3, MRS4149; 4, MRS4625; 5, MRS4626; 6, MRS4217; 7, MRS4525; 8, MRS4458.
Figure 4B:
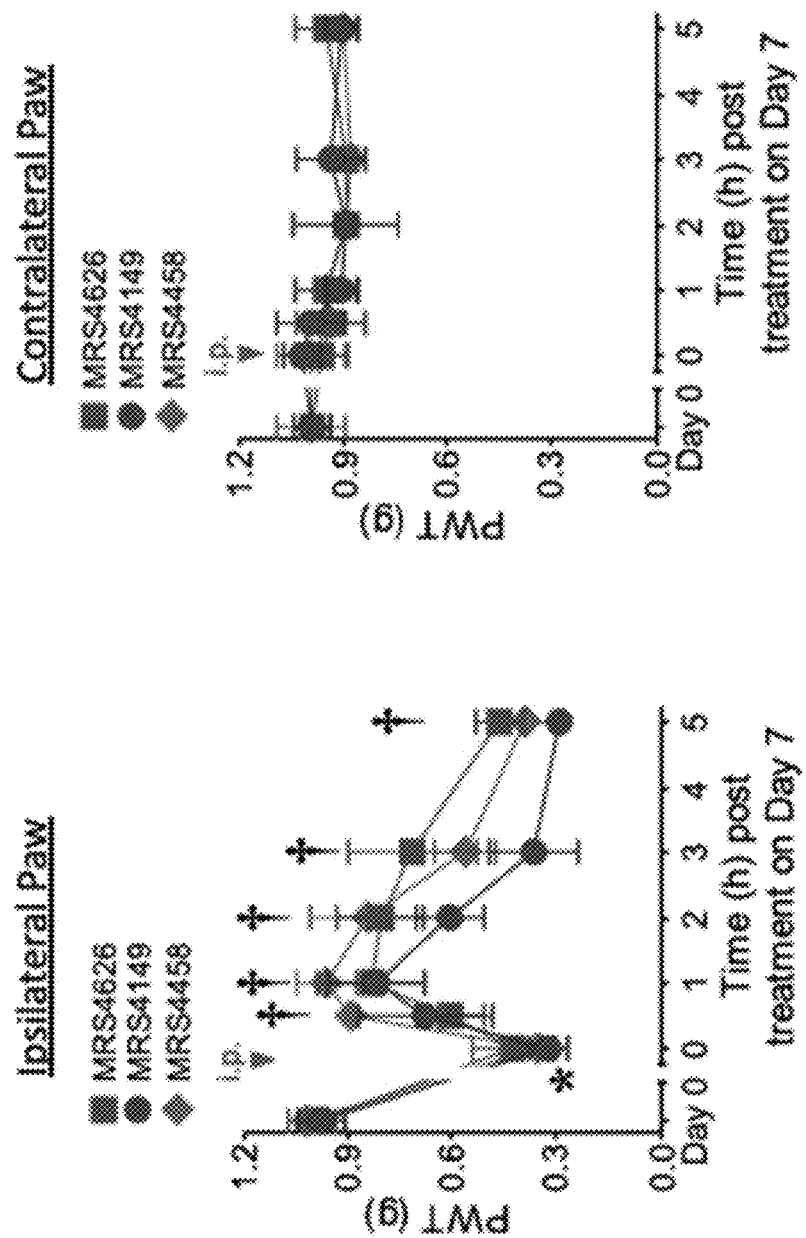
Figure 4C:
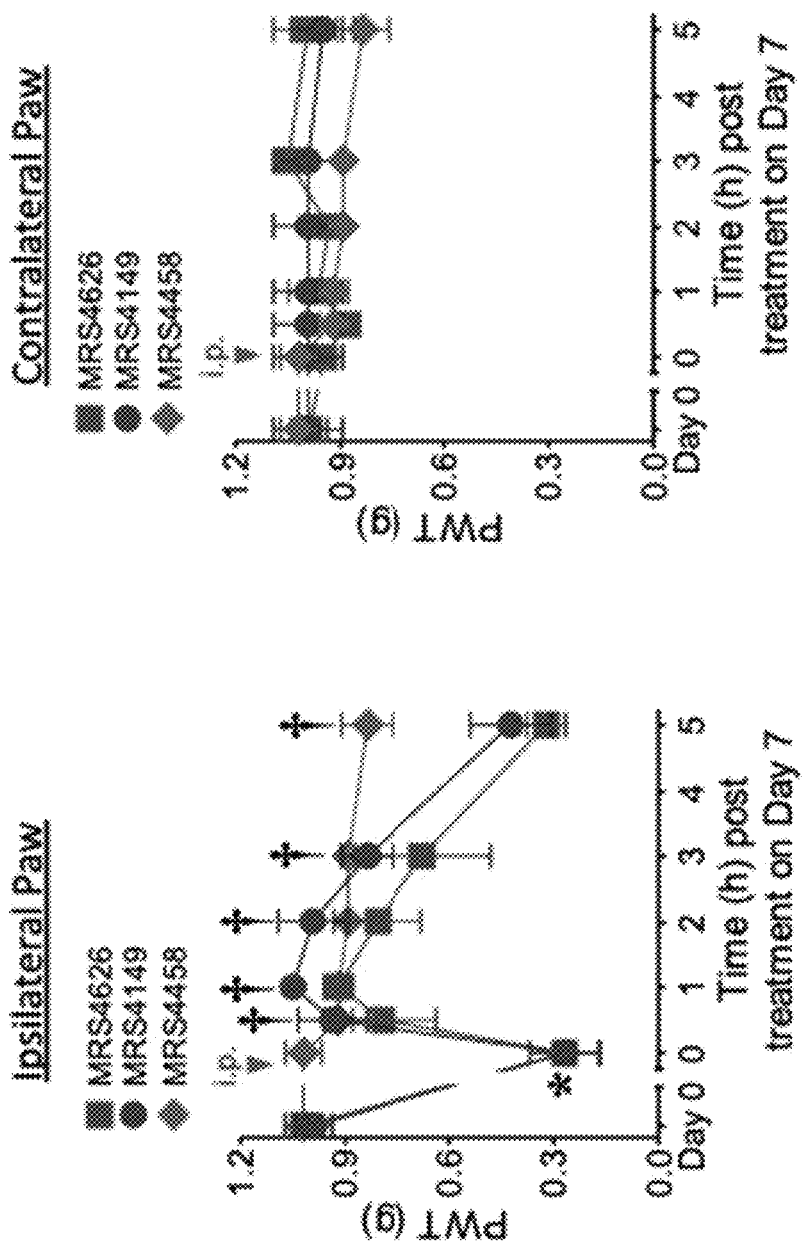
Figure 4D:
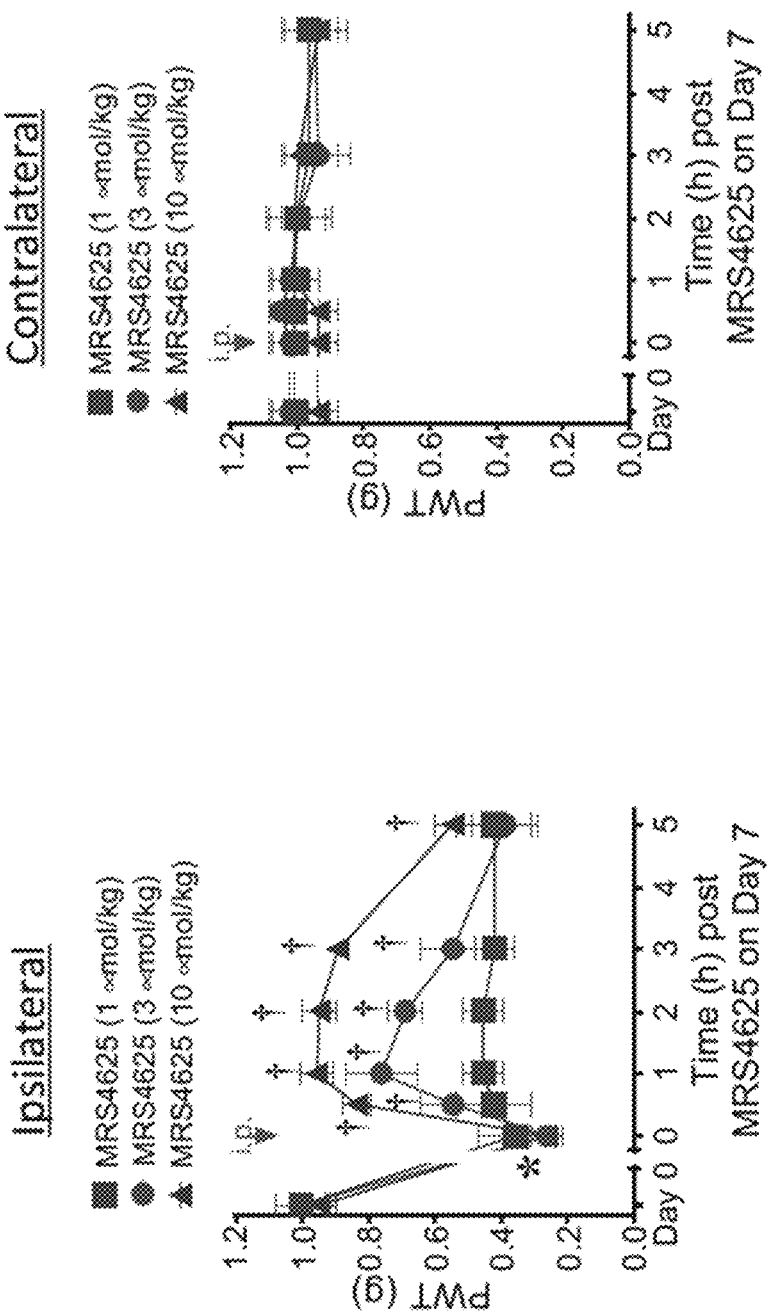
Figure 4E:
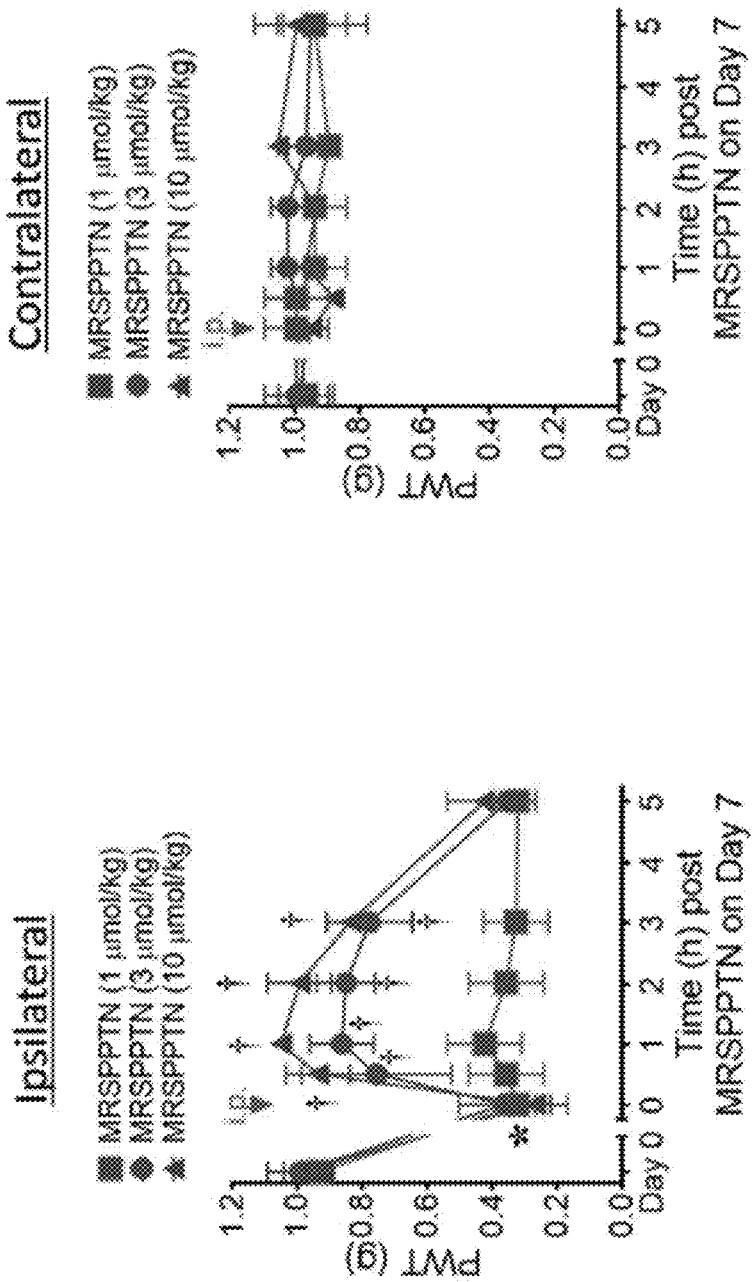
Figure 4F:
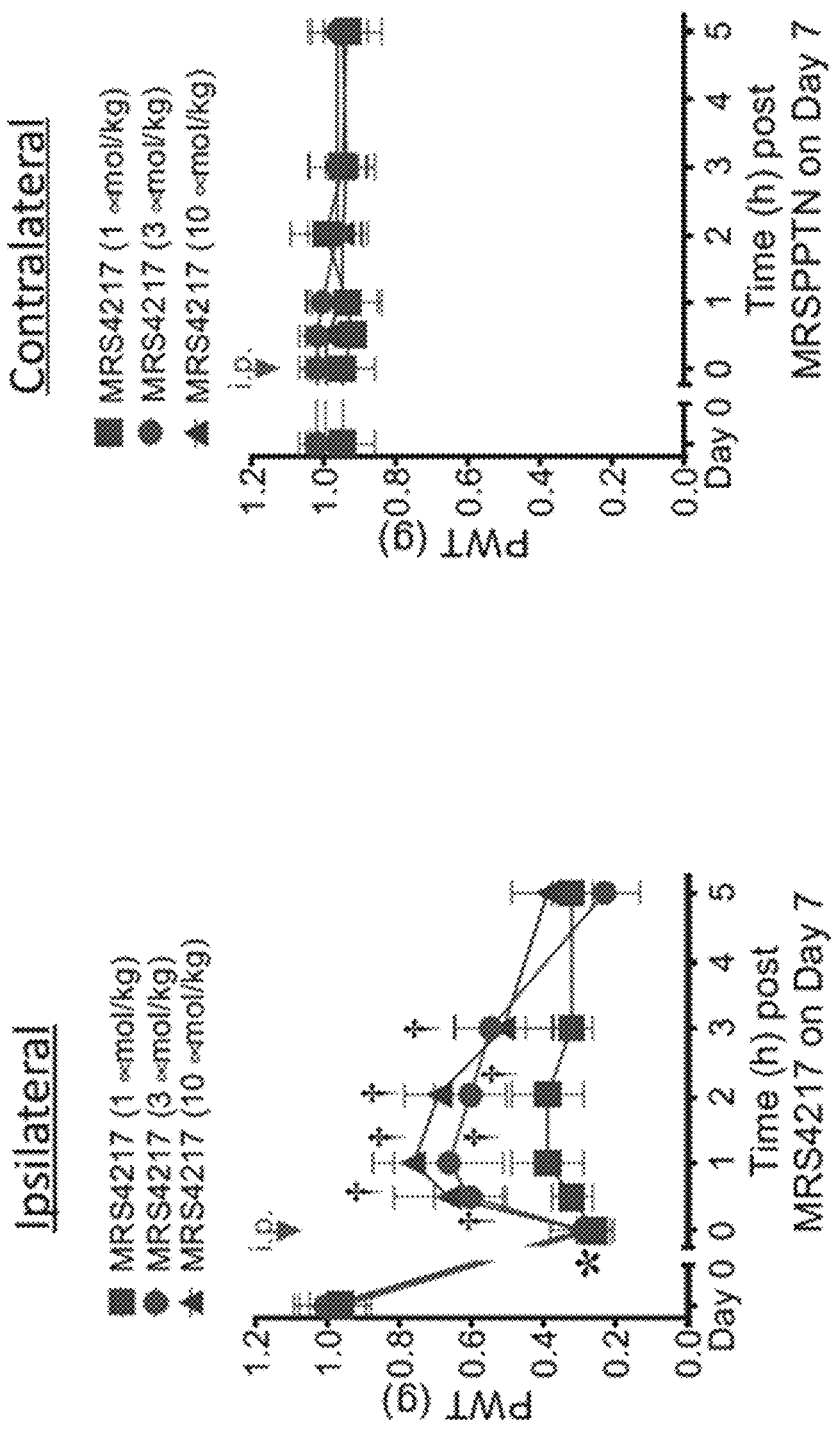

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

Disclosed are methods for treating neuropathic pain. Neuropathic pain is pain caused by damage or disease that affects the somatosensory system. It may be associated with abnormal sensations called dysesthesia, and pain produced by normally non-painful stimuli (allodynia). Neuropathic pain may have continuous and/or episodic (paroxysmal) components. The latter are likened to an electric shock. Common qualities include burning or coldness, "pins and needles" sensations, numbness and itching. Nociceptive pain, by contrast, is more commonly described as aching.

In one aspect, the present disclosure is directed to a method for treating neuropathic pain by administering to a subject in need thereof a P2Y14 antagonist.

As used herein, "subject in need thereof" (also used interchangeably herein with "a patient in need thereof") refers to a subject susceptible to or at risk of a specified disease, disorder, or condition. The methods disclosed herein can be used with a subset of subjects who are susceptible to or at elevated risk for neuropathic pain. Because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for certain diseases, disorders or conditions. Compounds of the present disclosure can be administered to "a subject in need thereof". As used herein, "a subject" (also interchangeably referred to as "an individual" and "a patient") refers to animals including humans and non-human animals. Accordingly, the compositions and methods disclosed herein can be used for human and veterinarian applications, particularly human and veterinarian medical applications. Suitable subjects include warm-blooded mammalian hosts, including humans, companion animals (e.g., dogs, cats), cows, horses, mice, rats, rabbits, primates, and pigs, preferably a human patient.

Suitable methods for administration of compounds of the present disclosure are by parenteral (e.g., intravenous (IV), intramuscular (IM), subcutaneous (SC), or intraperitoneal (IP)) routes and the formulations administered ordinarily include effective amounts of product in combination with acceptable diluents, carriers and/or adjuvants. Standard diluents such as human serum albumin are contemplated for pharmaceutical compositions of the disclosure, as are standard carriers as described herein.

Formulations for parenteral administration (e.g. by injection, for example bolus injection or continuous infusion) can be presented in unit dose form in ampoules, pre-filled syringes, small volume infusion or in multi-dose containers with and without an added preservative. The formulations can take such forms as suspensions, solutions, or emulsions in oily or aqueous vehicles, and may contain formulation agents such as suspending, stabilizing and/or dispersing agents.

As used herein, an "effective amount", a "therapeutically effective amount", a "prophylactically effective amount", and a "diagnostically effective amount" is the amount of the P2Y14 antagonist needed to elicit the desired biological response following administration. The amount of the P2Y14 antagonist will depend on the form the P2Y14 antagonist is in such as whether it is administered. Effective dosages are expected to vary substantially depending upon the P2Y14 antagonist used and the specific disease, disorder, or condition treated.

Suitable dosage can be determined by one of skill in the art and can also be adjusted by the individual physician in the event of any complication. Typically, the dosage of a composition comprising a P2Y14 antagonist can range from about 0.001 mg/kg body weight to about 5 g/kg body weight. In some embodiments, the dosage range ranges from about 0.001 mg/kg body weight to about 1 g/kg body weight, from about 0.001 mg/kg body weight to about 0.5 g/kg body weight, from about 0.001 mg/kg body weight to about 0.1 g/kg body weight, from about 0.001 mg/kg body weight to about 50 mg/kg body weight, from about 0.001 mg/kg body weight to about 25 mg/kg body weight, from about 0.001 mg/kg body weight to about 10 mg/kg body weight, from about 0.001 mg/kg body weight to about 5 mg/kg body weight, from about 0.001 mg/kg body weight to 1 about mg/kg body weight, from about 0.001 mg/kg body weight to about 0.1 mg/kg body weight, or from about 0.001 mg/kg body weight to about 0.005 mg/kg body weight. Alternatively, in some embodiments the dosage range is from 0.1 g/kg body weight to about 5 g/kg body weight, from about 0.5 g/kg body weight to about 5 g/kg body weight, from about 1 g/kg body weight to about 5 g/kg body weight, from about 1.5 g/kg body weight to about 5 g/kg body weight, from about 2 g/kg body weight to about 5 g/kg body weight, from about 2.5 g/kg body weight to about 5 g/kg body weight, from about 3 g/kg body weight to about 5 g/kg body weight, from about 3.5 g/kg body weight to about 5 g/kg body weight, from about 4 g/kg body weight to about 5 g/kg body weight, or from about 4.5 g/kg body weight to about 5 g/kg body weight. Suitable dosage for use in the methods of the present disclosure will depend upon a number of factors including, for example, age and weight of an individual, the specific disease, disorder, or condition treated, nature of a composition, route of administration and combinations thereof. Ultimately, a suitable dosage can be readily determined by one skilled in the art such as, for example, a physician, a veterinarian, a scientist, and other medical and research professionals. For example, one skilled in the art can begin with a low dosage that can be increased until reaching the desired treatment outcome or result. Alternatively, one skilled in the art can begin with a high dosage that can be decreased until reaching a minimum dosage needed to achieve the desired treatment outcome or result.

P2Y14 receptor (P2Y14-R, GPR105, and SC-GPR) is specifically activated by UDP-glucose and other nucleotide sugars (e.g., UDP-galactose, UDP-glucuronic acid. UDP-N-acetylglucosamine. UDP-glucuronic acid), and is sensitive to UDP, but not ADP/ATP and UTP. A suitable P2Y14 reference sequence includes the human P2Y14 amino acid sequence (NCBI reference sequence NP_001074924.1)

Suitable antagonists of P2Y14 include small molecule antagonists, for example. The term, "small molecule" is used herein according to its ordinary meaning as understood by those skilled in the art to refer to molecules having a molecular mass less than 5 kD. Suitable antagonists of P2Y14 include, for example, a 4,7-disubstituted naphthoic acid derivative such as, 4-[4-(piperidin-4-yl)phenyl]-7-[4-(rifluoromethyl)phenyl]-2-naphthoic acid (PPTN) (1).

Suitable antagonists of P2Y14 include analogues of PPTN (1) having a naphthalene or phenyl-triazolyl scaffold. Exemplary compounds include those having a formula of: formula (I), formula (II), formula (III), formula (IV), formula (V), and formula (VI), wherein (a) the compound of formula (I) is of the formula:

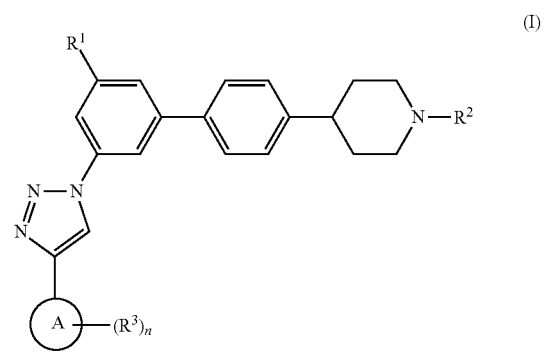

(I)

wherein ring A is aryl, heteroaryl, or cycloalkyl; $R^1$ is —$CO_2H$, —$CO_2(C_1\text{-}C_8$ alkyl), or a bioisostere of carboxylate; $R^2$ is H, $C_1\text{-}C_8$ alkyl, $C_2\text{-}C_8$ alkenyl, $C_2\text{-}C_8$ alkynyl, $C_3\text{-}C_6$ cycloalkyl, $C_3\text{-}C_6$ cycloalkylalkyl, hydroxyalkyl, $C_1\text{-}C_8$ haloalkyl, cyanoalkyl, aryl, heteroaryl, heterocycloalkyl, —$(CH_2)_m$aryl, —$(CH_2)_m$heteroaryl, or —$(CH_2)_m$heterocycloalkyl; each $R^3$ is independently $C_1\text{-}C_8$ alkyl, $C_2\text{-}C_8$ alkenyl, $C_3\text{-}C_6$ cycloalkyl, hydroxy, hydroxyalkyl, $C_1\text{-}C_8$ alkoxy, $C_3\text{-}C_6$ cycloalkyloxy, aryloxy, halo, $C_1\text{-}C_8$ haloalkyl, $C_1\text{-}C_8$ haloalkoxy, —CN, —$NO_2$, —$NR^5R^6$, —$C(O)R^4$, —$CO_2R^4$, —$C(O)NR^5R^6$, —$NR^5C(O)R^4$, —$(CH_2)_m$aryl, —$(CH_2)_m$heteroaryl, or —$(CH_2)_m$heterocycloalkyl; $R^4$, $R^5$, and $R^6$ are independently H or $C_1\text{-}C_8$ alkyl; and m and n are independently 0 or an integer from 1-5; or a pharmaceutically acceptable salt thereof; (b) the compound of formula (II) is of the formula:

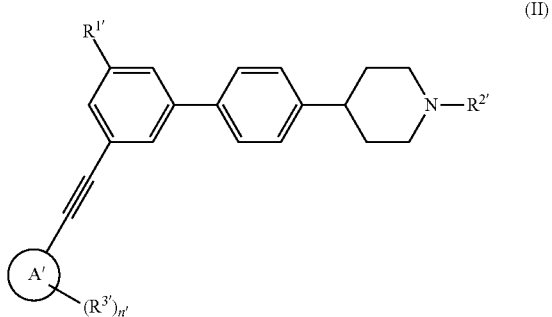

(II)

wherein ring A' is aryl, heteroaryl, or cycloalkyl; $R^{1'}$ is —$CO_2H$, —$C_2(C_1\text{-}C_8$ alkyl), or a bioisostere of carboxylate; $R^{2'}$ is H, $C_1\text{-}C_8$ alkyl, $C_2\text{-}C_8$ alkenyl, $C_2\text{-}C_8$ alkynyl, $C_3\text{-}C_6$ cycloalkyl, $C_3\text{-}C_6$ cycloalkylalkyl, hydroxyalkyl, $C_1\text{-}C_8$ haloalkyl, cyanoalkyl, aryl, heteroaryl, heterocycloalkyl, —$(CH_2)_m$aryl, —$(CH_2)_m$heteroaryl, or —$(CH_2)_m$heterocycloalkyl; each $R^{3'}$ is independently $C_1\text{-}C_8$ alkyl, $C_2\text{-}C_8$ alkenyl, $C_3$-$C_6$ cycloalkyl, hydroxy, hydroxyalkyl, $C_1$-$C_8$ alkoxy, $C_3$-$C_6$ cycloalkyloxy, aryloxy, halo, $C_1$-$C_8$ haloalkyl, $C_1$-$C_8$ haloalkoxy, —CN, —NO$_2$, —NR$^5$R$^{6'}$, —C(O)R$^{4'}$, —C$_2$R$^{4'}$, —C(O)NR$^5$R$^6$, —NR$^5$C(O)R$^{6'}$, —(CH$_2$)$_m$aryl, —(CH$_2$)$_m$heteroaryl, or —(CH$_2$)$_m$heterocycloalkyl; R$^{4'}$, R$^{5'}$, and R$^{6'}$ independently H or $C_1$-$C_8$ alkyl; and m' and n' are independently 0 or an integer from 1-5; or a pharmaceutically acceptable salt thereof; (c) the compound of formula (III) is a conjugate of the formula:

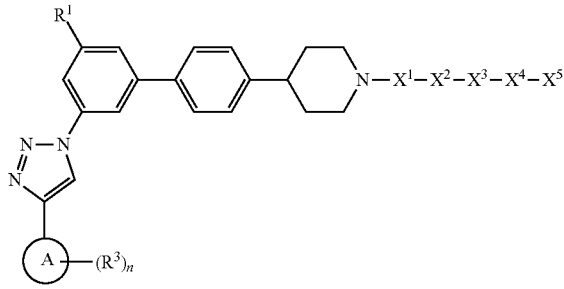

(III)

or a pharmaceutically acceptable salt thereof, wherein ring A is aryl, heteroaryl, or cycloalkyl; R$^1$ is —CO$_2$H, —CO$_2$($C_1$-$C_8$ alkyl) or a bioisostere of carboxylate; each R$^3$ is independently $C_1$-$C_8$ alkyl, $C_2$-$C_8$ alkenyl, $C_3$-$C_6$ cycloalkyl, hydroxy, hydroxyalkyl, $C_1$-$C_8$ alkoxy, $C_3$-$C_6$ cycloalkyloxy, aryloxy, halo, $C_1$-$C_8$ haloalkyl, $C_1$-$C_8$ haloalkoxy, —CN, —NO$_2$, —NR$^5$R$^6$, —C(O)R$^4$, —CO$_2$R$^4$, —C(O)NR$^5$R$^6$, —NR$^5$C(O)R$^4$, —(CH$_2$)$_m$aryl, —(CH$_2$)$_m$heteroaryl, or —(CH$_2$)$_m$heterocycloalkyl; R$^4$, R$^5$, and R$^6$ are independently H or $C_1$-$C_8$ alkyl; X$^1$ is selected from the group consisting of —(CH$_2$)$_o$—, —C(O)—, —C(O)NH—, —OC(O)NH—, —OC(O)—, —C(O)O—, —C(S)NH—, and —SO$_2$—; X$^2$ is selected from the group consisting of

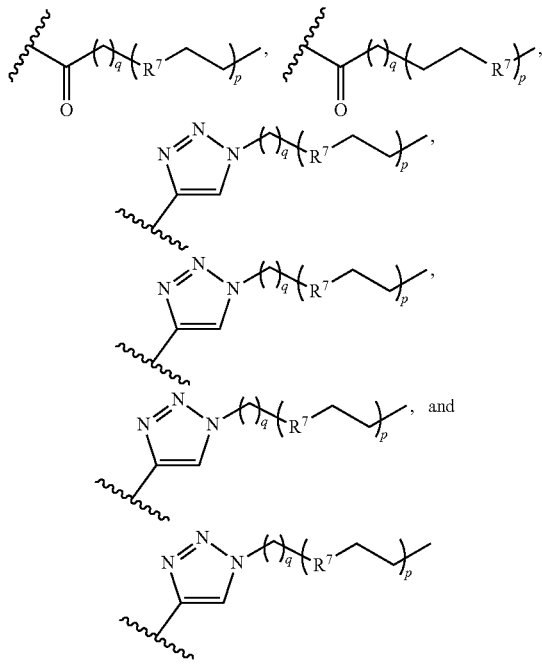

R$^7$ is CH$_2$, NH, or O; X$^4$ is selected from the group consisting of —(CH$_2$)$_o$—, —C(O)—, —C(O)NH—, —OC(O)NH—, —OC(O)—, —C(O)O—, —C(S)NH—, —SO$_2$—, —NHC(O)—, and

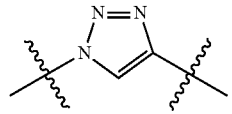 [SMILES: *c1cn(*)nn1]

X$^5$ is a reactive sulfur-containing moiety; m, n, and q are independently 0 or an integer from 1-5; o is an integer from 1-5; and p is 0 or an integer from 1-36; wherein X$^5$ is optionally linked to a particle; (d) the compound of formula (IV) is a dendron conjugate of the formula:

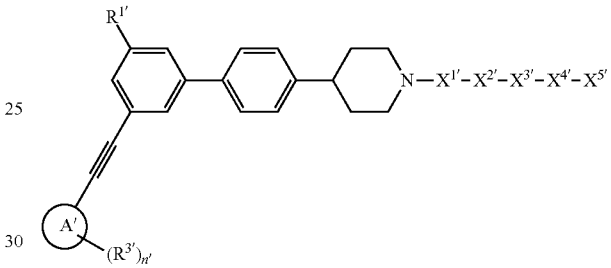

(IV)

or a pharmaceutically acceptable salt thereof, wherein ring A' is aryl, heteroaryl, or cycloalkyl; R$^{1'}$ is —CO$_2$H, —CO$_2$($C_1$-$C_8$ alkyl), or a bioisostere of carboxylate; each R$^{3'}$ is independently $C_1$-$C_8$ alkyl, $C_2$-$C_8$ alkenyl, $C_3$-$C_6$ cycloalkyl, hydroxy, hydroxyalkyl, $C_1$-$C_8$ alkoxy, $C_3$-$C_6$ cycloalkyloxy, aryloxy, halo, $C_1$-$C_8$ haloalkyl, $C_1$-$C_8$ haloalkoxy, —CN, —NO$_2$, —NR$^5$R$^{6'}$, —C(O)R$^{4'}$, —CO$_2$R$^{4'}$, —C(O)NR$^5$R$^6$, —NR$^5$C(O)R$^{4'}$, —(CH$_2$)$_m$aryl, —(CH$_2$)$_m$heteroaryl, or —(CH$_2$)$_m$heterocycloalkyl; R$^{4'}$, R$^{5'}$, and R$^{6'}$ are independently H or $C_1$-$C_8$ alkyl; X$^{1'}$ is selected from the group consisting of —(CH$_2$)$_{o'}$—, —C(O)—, —C(O)NH—, —OC(O)NH—, —OC(O)—, —C(O)O—, —C(S)NH—, and —SO$_2$—; X$^{2'}$ is selected from the group consisting of

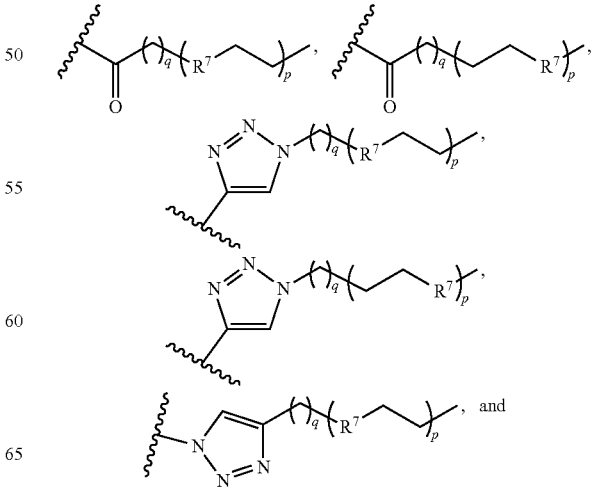

-continued

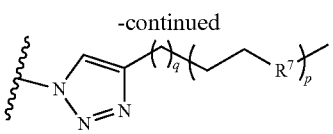

R⁷ is CH₂, NH, or O; X³' is a dendron; X⁴' is selected from the group consisting of —(CH₂)$_{o'}$—, —C(O)—, —C(O)NH—, —OC(O)NH—, —OC(O)—, —C(O)O—, —C(S)NH—, —SO₂—, —NH—C(O)—, and

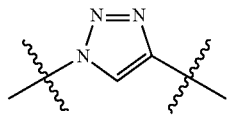 [SMILES: *c1cn(*)nn1]

X⁵' is a reactive sulfur-containing moiety; m', n', and q' are the same or different and each is 0 or an integer from 1-5; o' is an integer from 1-5; and p' is 0 or an integer from 1-36; wherein X⁵' is optionally linked to a particle; (e) the compound of formula (V) is of the formula:

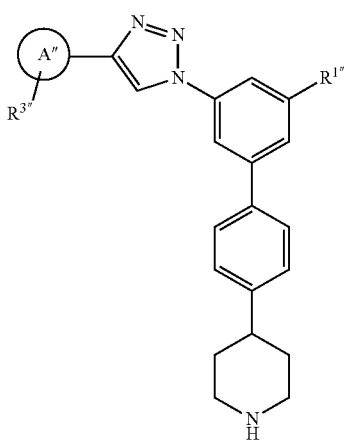

(V)

ring A" is aryl, heteroaryl, or cycloalkyl; R¹" is —C₂H, —CO₂(C₁-C₈ alkyl), or a bioisostere of carboxylate; R³" is C₁-C₈ alkyl, C₂-C₈ alkenyl, C₃-C₆ cycloalkyl, hydroxy, hydroxyalkyl, C₁-C₈ alkoxy, C₃-C₆ cycloalkyloxy, aryloxy, halo, C₁-C₈ haloalkyl, C₁-C₈ haloalkoxy, —CN, —NO₂, —NR⁵'R⁶', —C(O)R⁴', —CO₂R⁴', —C(O)NR⁵'R⁶', —NR⁵'C(O)R⁴', —(CH₂)$_m$aryl, —(CH₂)$_m$heteroaryl, or —(CH₂)$_m$heterocycloalkyl; R⁴, R⁵, and R⁶ are each independently H or C₁-C₈ alkyl; and m and n are each independently 0 or an integer from 1-5; or a pharmaceutically acceptable salt thereof; and (f) the compound (VI) is of the formula:

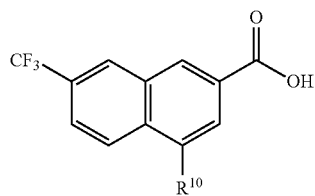

(VI)

or a pharmaceutically acceptable salt thereof, wherein R¹⁰ is selected from the group consisting of hydroxyl and

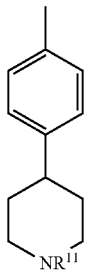

R¹¹ is hydrogen, C₁-C₈ alkoxy, and C₂-C₈ alkyne.

Ring A of formula (I) or formula (V) can be phenyl, furanyl, thiazolyl, thienyl, pyrazolyl, pyridazinyl, pyridinyl, pyrazinyl, benzofuranyl, cyclopropyl, or cyclohexyl, or a pharmaceutically acceptable salt thereof.

Suitably, R¹ of formula (I) or formula (V) can be —CO₂H, or a pharmaceutically acceptable salt thereof.

Suitably, R¹ of formula (I) can be a bioisostere of carboxylate selected from

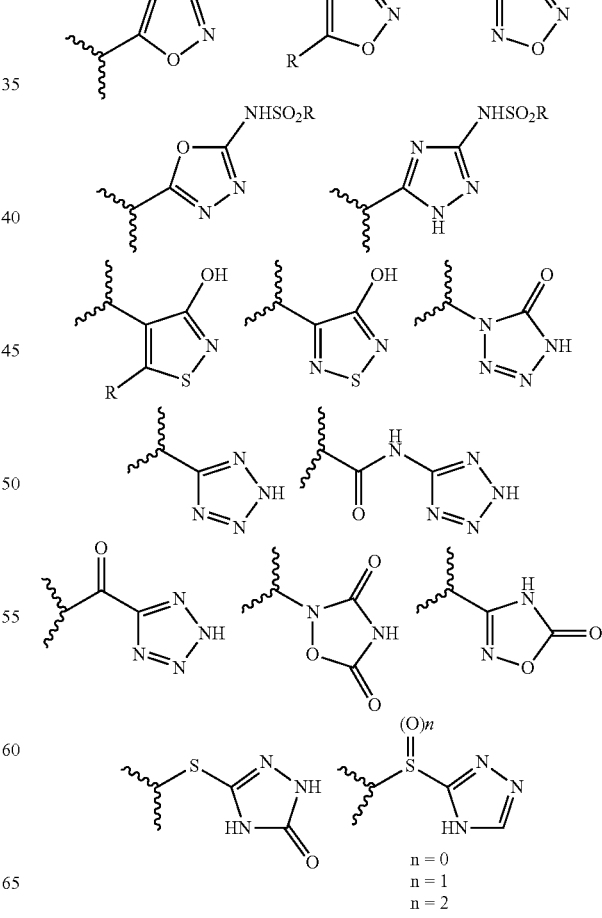

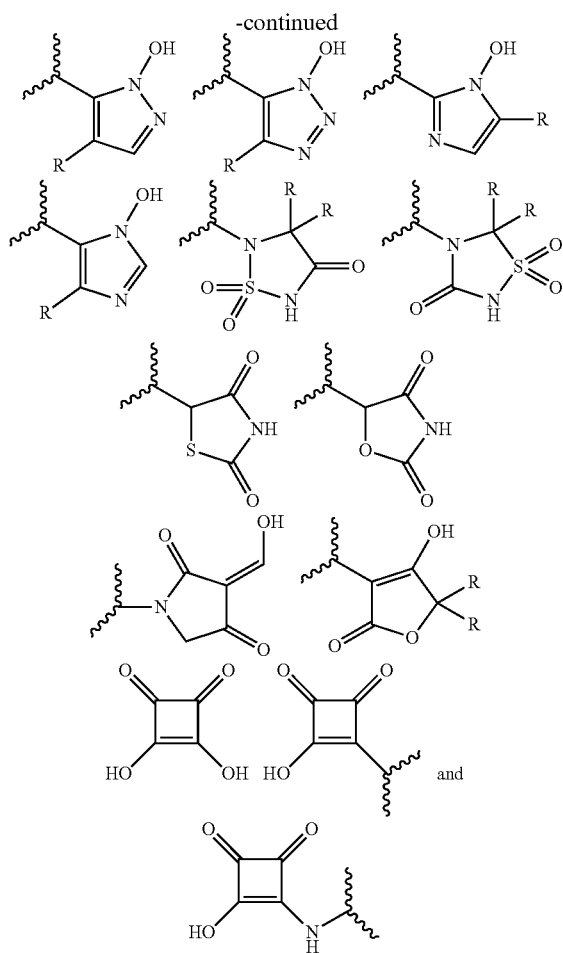

or a pharmaceutically acceptable salt thereof.

Suitably, $R^2$ of formula (I) can be H or $C_2$-$C_8$ alkynyl, or a pharmaceutically acceptable salt thereof.

Suitably, $R^3$ is $C_1$-$C_8$ alkyl, hydroxy, hydroxyalkyl, $C_1$-$C_8$ alkoxy, halo, $C_1$-$C_8$ haloalkyl, $C_1$-$C_8$ haloalkoxy, —CN, —NH$_2$, —CO$_2$R$^4$, or a pharmaceutically acceptable salt thereof.

The compound of formula (II) is of the formula:

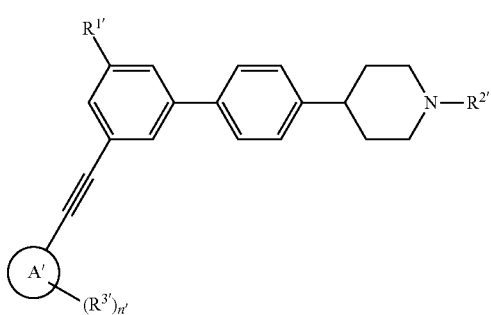

(II)

wherein ring A' is aryl, heteroaryl, or cycloalkyl; $R^{1'}$ is —CO$_2$H—, —CO$_2$(C$_1$-C$_8$ alkyl), or a bioisostere of carboxylate; $R^{2'}$ is H, $C_1$-$C_8$ alkyl, $C_2$-$C_8$ alkenyl, $C_2$-$C_8$ alkynyl, $C_3$-$C_6$ cycloalkyl, $C_3$-$C_6$ cycloalkylalkyl, hydroxyalkyl, $C_1$-$C_8$ haloalkyl, cyanoalkyl, aryl, heteroaryl, heterocycloalkyl, —(CH$_2$)$_m$aryl, —(CH$_2$)$_m$heteroaryl, or —(CH$_2$)$_m$heterocycloalkyl; each $R^{3'}$ is the same or different and each is $C_1$-$C_8$ alkyl, $C_2$-$C_8$ alkenyl, $C_3$-$C_6$ cycloalkyl, hydroxy, hydroxyalkyl, $C_1$-$C_8$ alkoxy, $C_3$-$C_6$ cycloalkyloxy, aryloxy, halo, $C_1$-$C_8$ haloalkyl, $C_1$-$C_8$ haloalkoxy, —CN, —NO$_2$, —NR$^{5'}$R$^{6'}$, —C(O)R$^{4'}$, —CO$_2$R$^{4'}$, —C(O)NR$^{5'}$R$^{6'}$, —NR$^{5'}$C(O)R$^{4'}$, —(CH$_2$)$_m$aryl, —(CH$_2$)$_m$heteroaryl, or —(CH$_2$)$_m$heterocycloalkyl; $R^{4'}$, $R^{5'}$, and $R^{6'}$ are the same or different and each is H or $C_1$-$C_8$ alkyl; and m' and n' are the same or different and each is 0 or an integer from 1-5; or a pharmaceutically acceptable salt thereof.

Suitably, the compound used in the method is a conjugate of formula (III) or a pharmaceutically acceptable salt thereof, wherein ring A is aryl, heteroaryl, or cycloalkyl; $R^1$ is —CO$_2$H, —CO$_2$(C$_1$-C$_8$ alkyl), or a bioisostere of carboxylate; each $R^3$ is the same or different and each is $C_1$-$C_8$ alkyl, $C_2$-$C_8$ alkenyl $C_3$-$C_6$ cycloalkyl, hydroxy, hydroxyalkyl, $C_1$-$C_8$ alkoxy, $C_6$-$C_6$ cycloalkyloxy, aryloxy, halo, $C_1$-$C_8$ haloalkyl, $C_1$-$C_8$ haloalkoxy, —CN, —NO$_2$, —NR$^5$R$^6$, —C(O)R$^4$, —CO$_2$R$^4$, —C(O)NR$^5$R$^6$, —NR$^5$C(O)R$^4$, —(CH$_2$)$_m$aryl, —(CH$_2$)$_m$heteroaryl, or —(CH$_2$)$_m$heterocycloalkyl; $R^4$, $R^5$, and $R^6$ are the same or different and each is H or $C_1$-$C_8$ alkyl; $X^1$ is selected from the group consisting of —(CH$_2$)$_o$—, —C(O)—, —C(O)NH—, —OC(O)NH—, —C(O)—, —C(O)O—, —C(S)NH—, and —SO$_2$—; $X^2$ is selected from the group consisting of

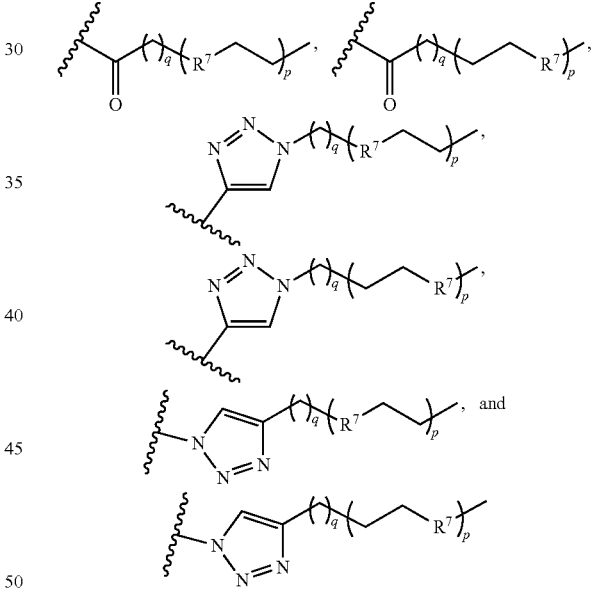

wherein $R^7$ is CH$_2$, NH, or O; $X^3$ is a dendron; $X^4$ is selected from the group consisting of —(CH$_2$)o-, —C(O)—, —C(O)NH—, —OC(O)NH—, —OC(O)—, —C(O)O—, —C(S)NH—, —SO—, —NHC(O)—, and

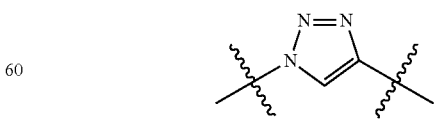

$X^5$ is a reactive sulfur-containing moiety; m, n, and q are the same or different and each is 0 or an integer from 1-5; o is an integer from 1-5; and p is 0 or an integer from 1-36; wherein $X^5$ is optionally linked to a particle.

Suitably, in formula (III), the dendron is carboxyethylpolyamido (CEPAM) dendron that is optionally functionalized in at least one position to include the moiety

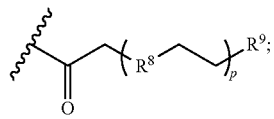

wherein $R^8$ is $CH_2$, NH, or O, and $R^9$ is —$NH_2$ or —$CO_2H$.

The compound used in the method suitably can be a dendron conjugate of formula (IV) or a pharmaceutically acceptable salt thereof, wherein ring A' is aryl, heteroaryl, or cycloalkyl; $R^{1'}$ is —$CO_2H$, —$CO_2(C_1-C_8$ alkyl), or a bioisostere of carboxylate; $R^{2'}$ is H, $C_1-C_8$ alkyl, $C_2-C_8$ alkenyl, $C_2-C_8$ alkynyl, $C_3-C_6$ cycloalkyl, $C_3-C_6$ cycloalkylalkyl, hydroxyalkyl, $C_1-C_8$ haloalkyl, cyanoalkyl, aryl, heteroaryl, heterocycloalkyl, —$(CH_2)_m$aryl, —$(CH_2)_m$heteroaryl, or —$(CH_2)_m$heterocycloalkyl; each $R^{3'}$ is the same or different and each is $C_1-C_8$ alkyl, $C_2-C_8$ alkenyl, $C_3-C_6$ cycloalkyl, hydroxy, hydroxyalkyl, $C_1-C_8$ alkoxy $C_3-C_6$ cycloalkyloxy, aryloxy, halo, $C_1-C_8$ haloalkyl, $C_1-C_8$ haloalkoxy —CN, —$NO_2$, —$NR^{5'}R^{6'}$, —$C(O)R^{4'}$, —$CO_2R^{4'}$, —$C(O)NR^{5'}R^{6'}$, —$NR^{5'}C(O)R^{4'}$, —$(CH_2)_m$aryl, —$(CH_2)_m$heteroaryl, or —$(CH_2)_m$heterocycloalkyl; $R^{4'}$, $R^{5'}$, and $R^{6'}$ are the same or different and each is H or $C_1-C_8$ alkyl; $X^{1'}$ is selected from the group consisting of —$(CH_2)_{o'}$—, —C(O)—, —C(O)NH—, —OC(O)NH—, —OC(O)—, —C(O)O—, —C(S)NH—, and —$SO_2$—; $X^{2'}$ is selected from the group consisting of

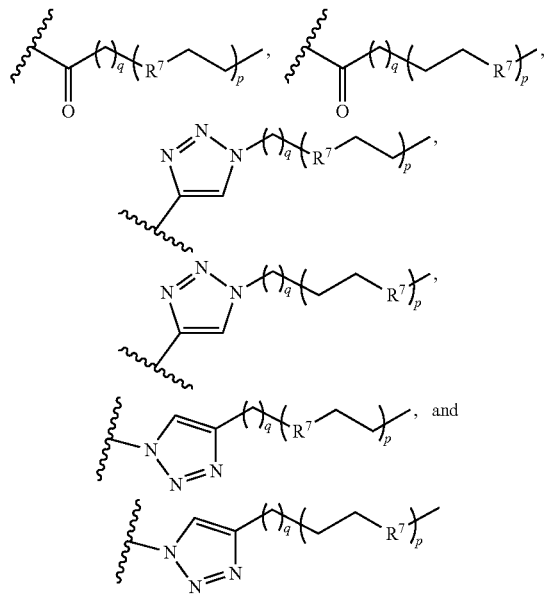

$R^{7'}$ is $CH_2$, NH, or O; $X^{3'}$ is a dendron; $X^{4'}$ is selected from the group consisting of —$(CH_2)_{o'}$—, —C(O)—, —C(O)NH—, —OC(O)NH—, —OC(O)—, —C(O)O—, —C(S)NH—, —$SO_2$— —NHC(O)—, and

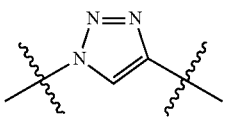 [SMILES: *c1cn(*)nn1]

$X^{5'}$ is a reactive sulfur-containing moiety; m', n', and q' are the same or different and each is 0 or an integer from 1-5; o' is an integer from 1-5; and p' is 0 or an integer from 1-36; wherein $X^{5'}$ is optionally linked to a particle.

Suitably, the R3" of formula (V) or (VI) is $CF_3$.

These and similar analogues of PPTN are described more fully in U.S. Pat. No. 10,683,277 (Jacobson et al., Jun. 16, 2020), which is hereby incorporated by reference to the extent it is consistent herewith.

In particular embodiments, small molecule antagonists of P2Y14 include, for example,

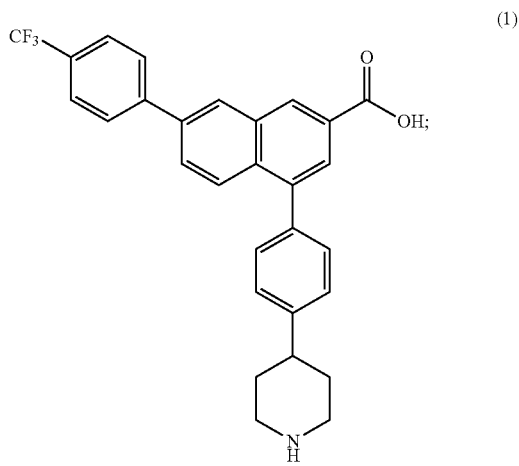

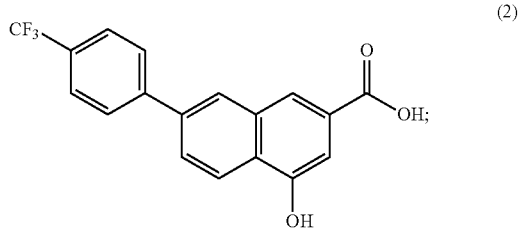

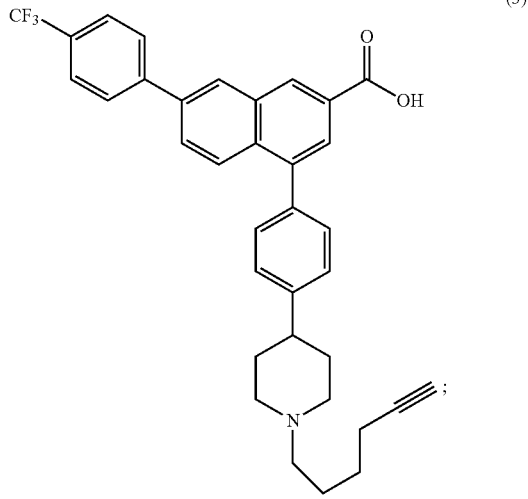

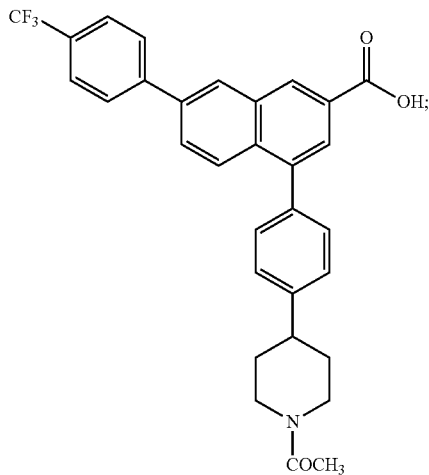
(4)
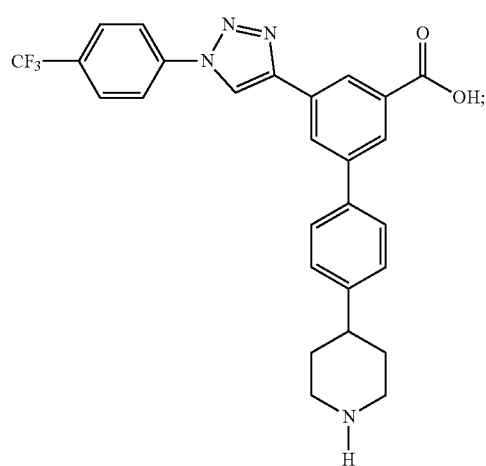
(7)
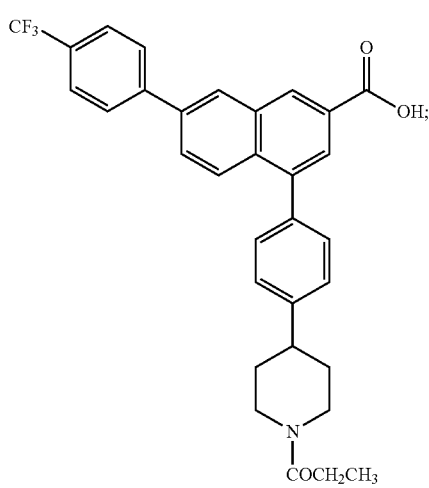
(5)
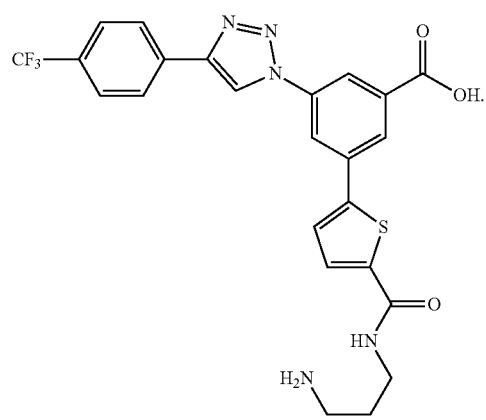
(8)
Other suitable P2Y14 antagonists for use in the present disclosure include those taught and described in WO 2019/157417 (Jacobson et al., Aug. 15, 2019), which have the general formula:
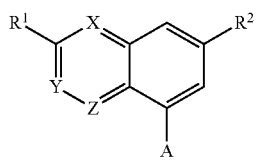
wherein (i) X is N, Y is CH, and Z is CH, (ii) X is CH, Y is N, and Z is CH, or (iii) X is CH.
Y is CH, and Z is N.
R¹ is halo or trifluormethyl,
R² is COOH, CN, CONH₂, or
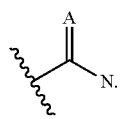
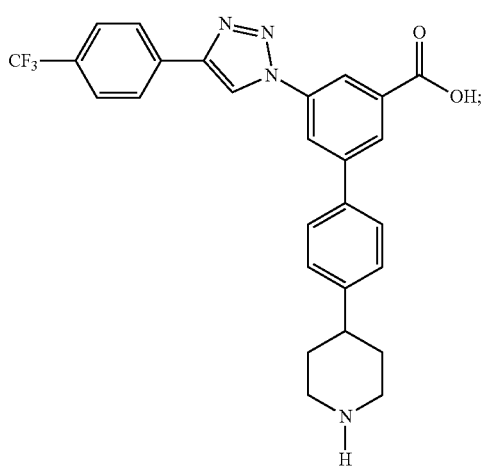
(6)

A is selected from die group consisting of
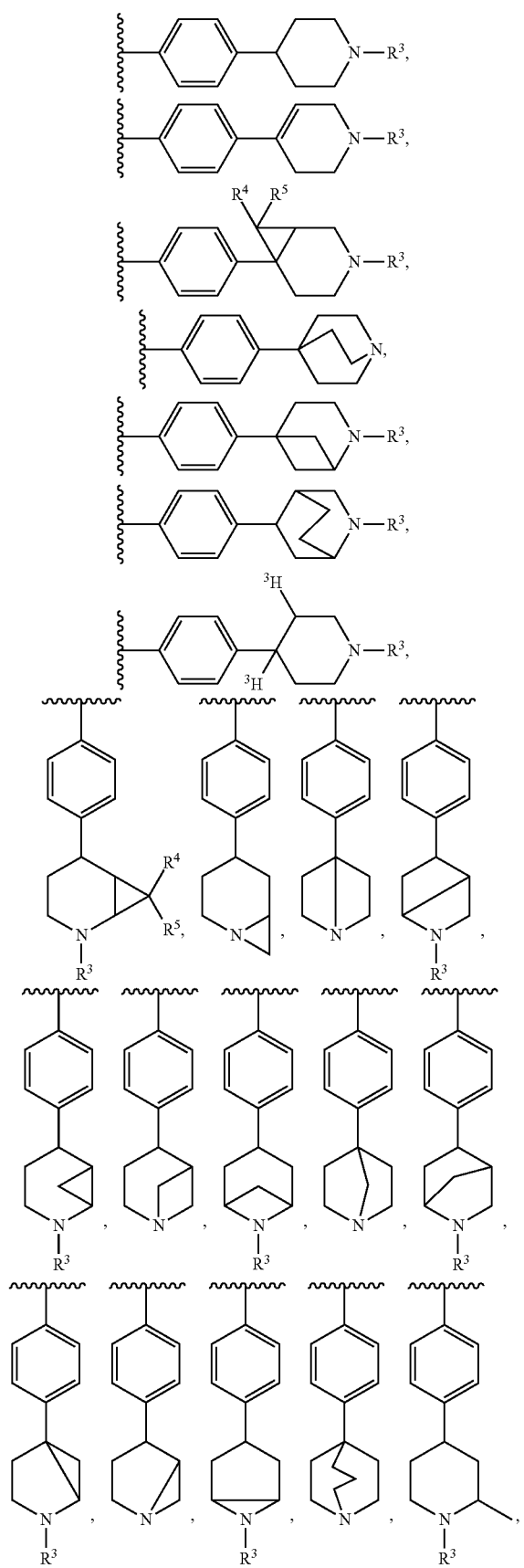
-continued
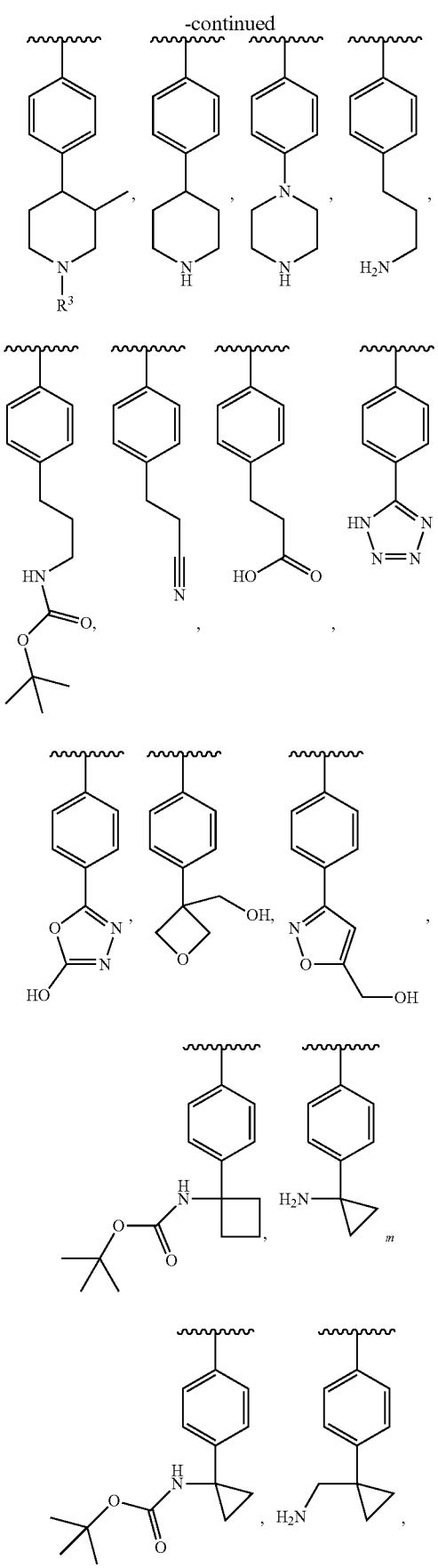

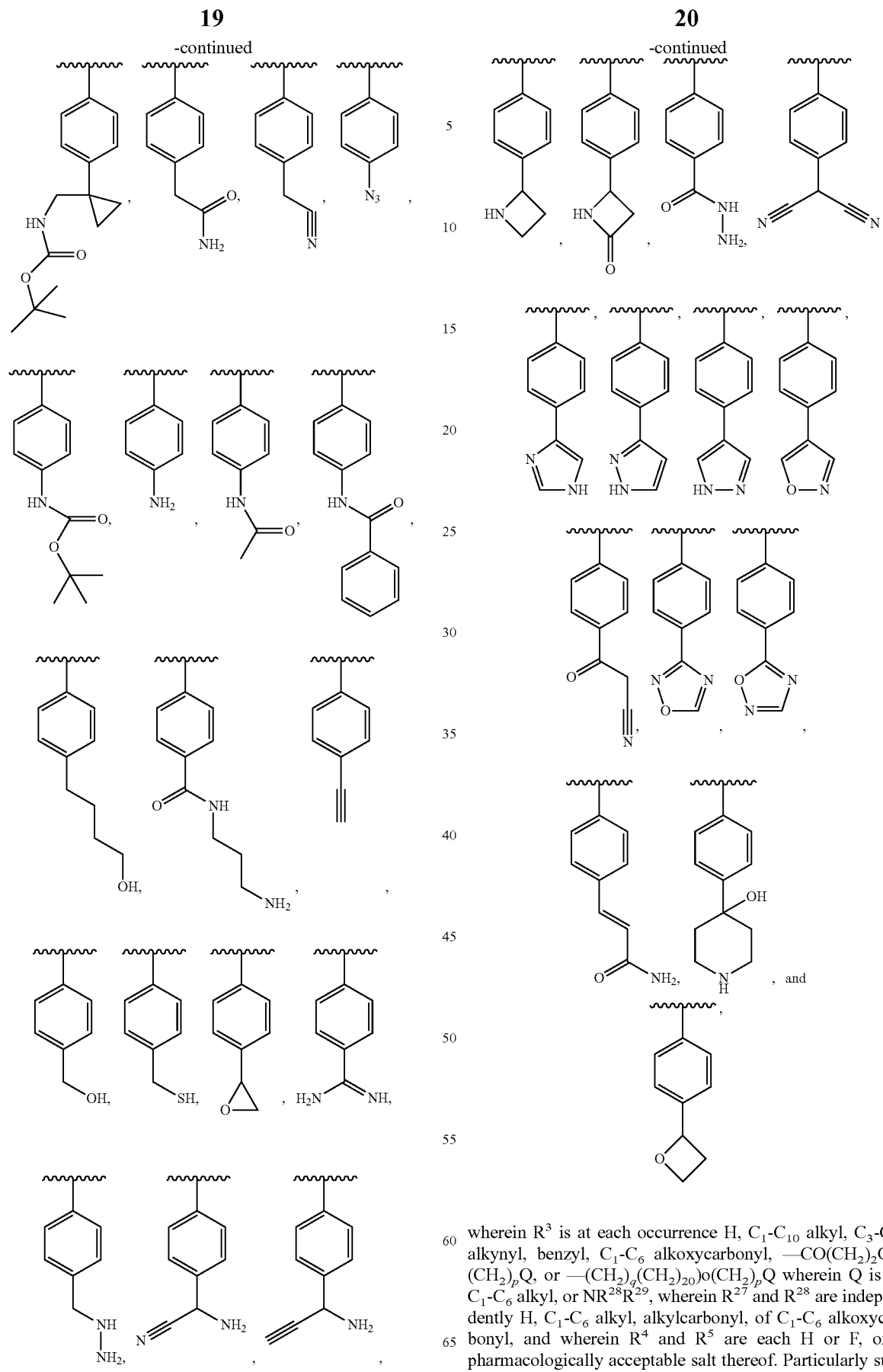

wherein $R^3$ is at each occurrence H, $C_1$-$C_{10}$ alkyl, $C_3$-$C_{10}$ alkynyl, benzyl, $C_1$-$C_6$ alkoxycarbonyl, —CO(CH$_2$)$_2$O)o(CH$_2$)$_p$Q, or —(CH$_2$)$_q$(CH$_2$)$_{20}$)o(CH$_2$)$_p$Q wherein Q is H, $C_1$-$C_6$ alkyl, or NR$^{28}$R$^{29}$, wherein $R^{27}$ and $R^{28}$ are independently H, $C_1$-$C_6$ alkyl, alkylcarbonyl, of $C_1$-$C_6$ alkoxycarbonyl, and wherein $R^4$ and $R^5$ are each H or F, or a pharmacologically acceptable salt thereof. Particularly suitable compounds include those compounds of the formulas:

21
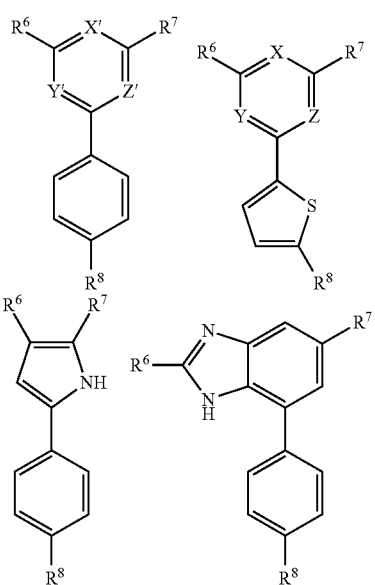
wherein R⁶ is selected from the group consisting of
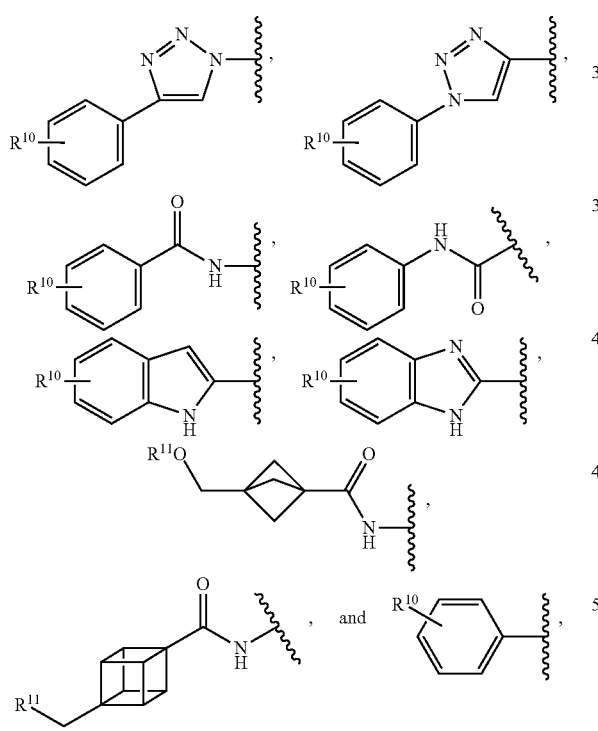
$R^7$ is COOH, CONH$_2$, CN,
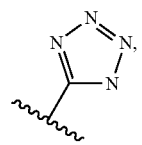 [SMILES: *c1nnn[nH]1]
or COCH$_2$NMe$_2$,
22
$R^8$ is selected from the group consisting of C1-C10 alkyl, —CONHR$_{12}$R$_{13}$, —CONH(CH$_2$)$_m$—NHR$_{14}$R$_{15}$.
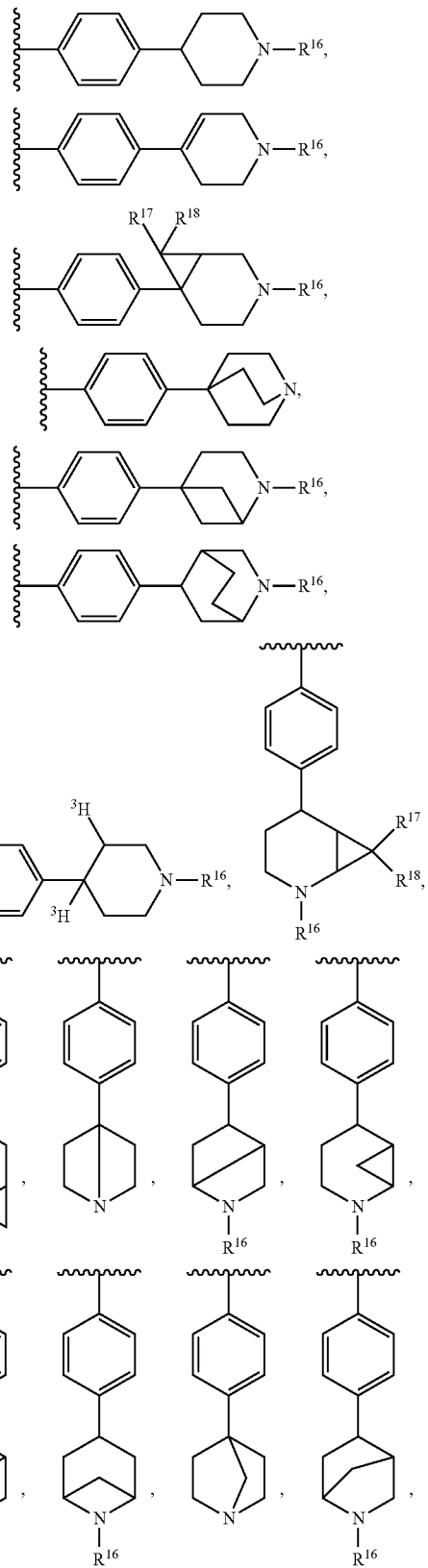

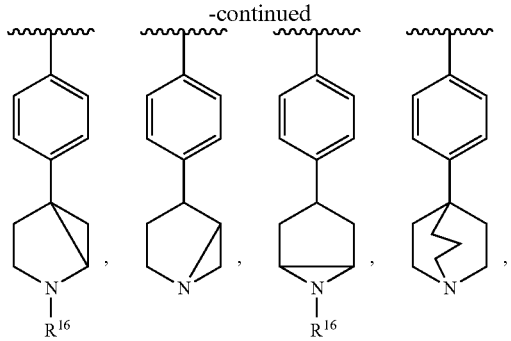
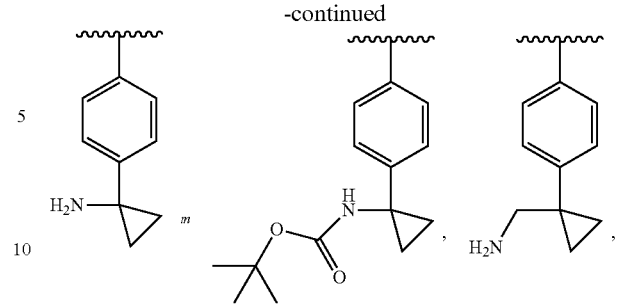
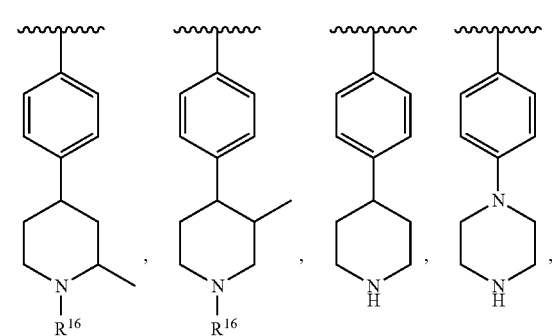
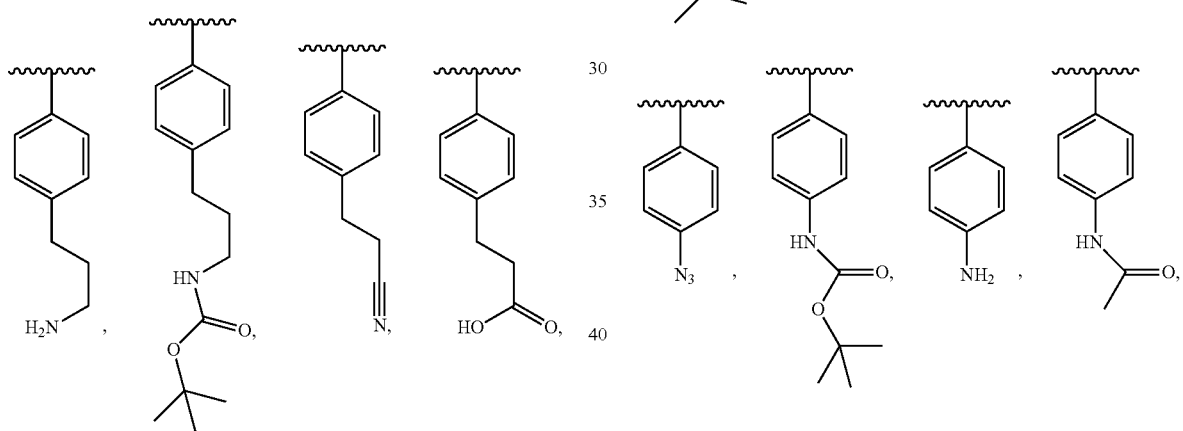
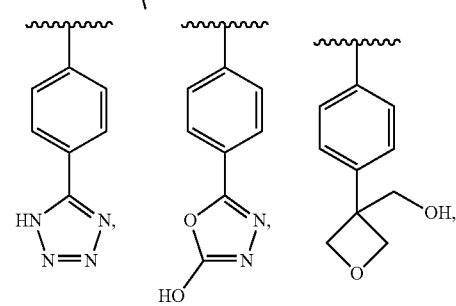
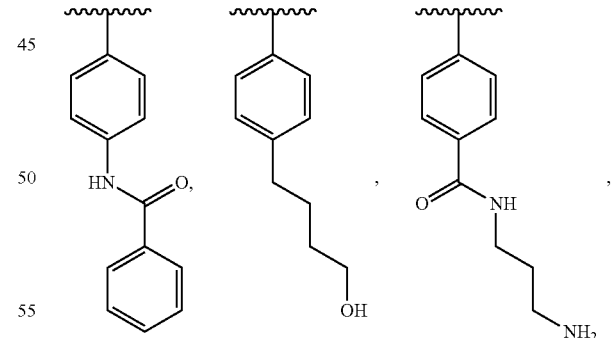
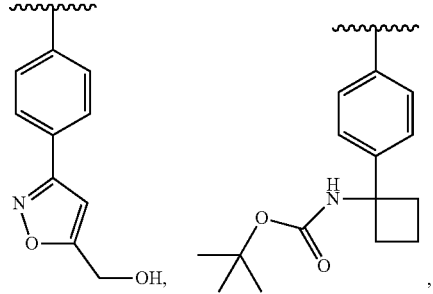
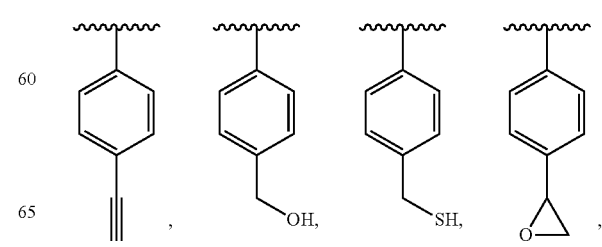

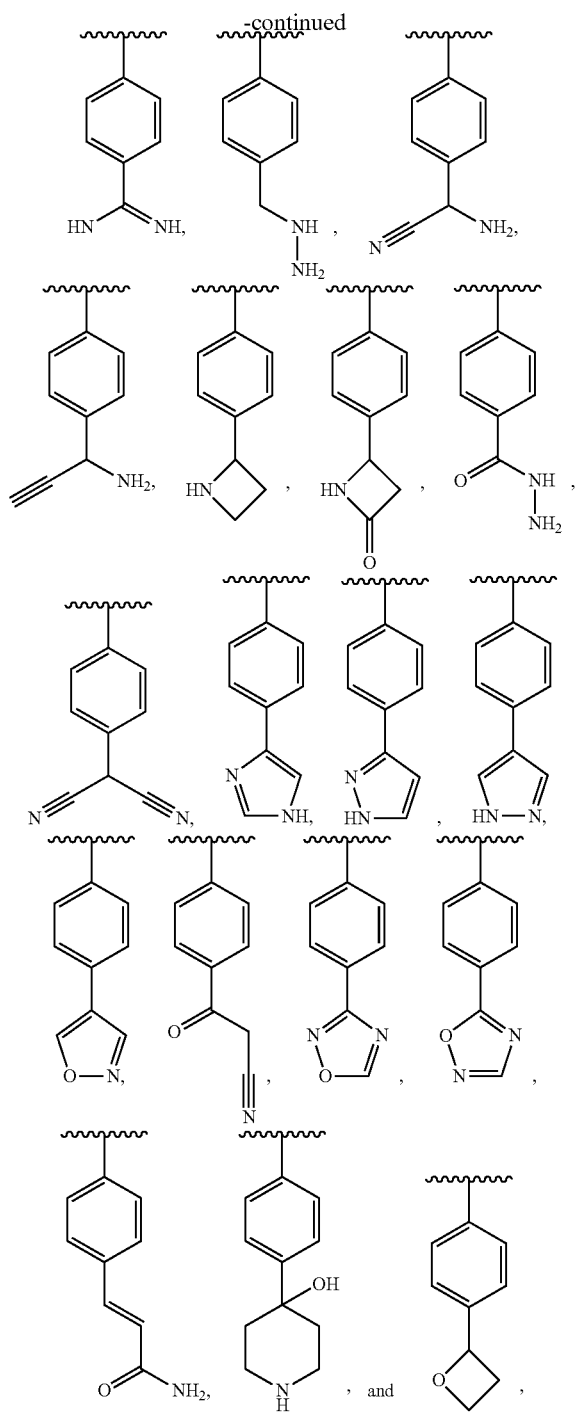

R$^{10}$ is halo or CF$_3$,
R$^{11}$ is halo, OH, or Ci-C$_6$ alkoxy,
R$^{12}$ and R$^{13}$ are independently H or Ci-C$_6$ alkyl,
R$^{14}$ and R$^{15}$ are independently H or Ci-C$_6$ alkyl,
R$^{16}$ is H, C1-C10 alkyl, or C3-C10 alkynyl, and
R$^{17}$ and R$^{18}$ are both H or both F,
m is an integer of from 1 to about 10,
(i) X is N, Y is CH, and Z is CH, (ii) X is CH, Y is N, and Z is CH, or (iii) X is CH, Y is CH, and Z is N,
X' and Y' are CH or N, and
Z' is N or CR$^9$ wherein R$^9$ is H or C$_1$-C$_6$ alkyl,
or a pharmaceutically acceptable salt thereof.

The disclosure of the above compounds are hereby incorporated by reference to the extent they are consistent with the present disclosure.

Suitable large molecule antagonists of P2Y14 include, for example, antibodies and antibody fragments that specifically bind P2Y14. Suitable P2Y14 antibodies include commercially available P2Y14 antibodies available from Alomone Labs (Jerusalem, Israel), Invitrogen, Sigma Aldrich, Merck Millipore and. Suitable antibodies include, for example, polyclonal, monoclonal, chimeric, humanized, recombinant, single chain, F$_{ab}$, F$_{at}$, F$_{sc}$, P$_{vv}$, and F$_{(ab')2}$ fragments. In some embodiments, neutralizing antibodies can be used as inhibitors of P2Y4. Suitable antibodies include, for example, 5A3F1, 8A11B11, PA5-77676, PA5-34089, OPA1-15556, PA5-34088, PA5-34087, and PA5-96964.

Suitable routes of administration include oral, sublingual, transdermal, subcutaneous, topical, absorption through epithelial or mucocutaneous linings, intravenous, intranasal, intraarterial, intramuscular, intratumoral, peritumoral, interperitoneal, intrathecal, rectal, vaginal, or aerosol formulations. In some aspects, the pharmaceutical composition including one or more of the above antagonist is administered orally or intravenously.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound of formula (I) or (II) or a salt thereof can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

EXAMPLES

Example 1

In this Example, eight P2Y14R antagonists, including three newly synthesized analogues containing a naphthalene or phenyl-triazolyl scaffold, were compared in a mouse model of chronic neuropathic pain (sciatic constriction).

Materials & Methods

Chemical

Reagents and instrumentation. All reagents and solvents were purchased from Sigma-Aldrich (St. Louis, Mo.). 1H NMR spectra were obtained with a Bruker 400 spectrometer using CDCl3, CD3OD, and DMSO-d$_6$ as solvents. Chemical shifts are expressed in δ values (ppm) with tetramethylsilane (δ 0.00) for CDCl$_3$ and water (δ 3.30) for CD$_3$OD. NMR spectra were collected with a Bruker AV spectrometer equipped with a z-gradient [$^1$H, $^{13}$C, $^{15}$N]-cryoprobe. TLC analysis was carried out on glass sheets precoated with silica gel F254 (0.2 mm) from Sigma-Aldrich. The purity of final compounds was checked using a Hewlett-Packard 1100

HPLC equipped with a Zorbax SB-Aq 5 μm analytical column (50×4.6 mm; Agilent Technologies Inc., Palo Alto, Calif.). Mobile phase: linear gradient solvent system, 5 mM tetrabutylammonium dihydrogen phosphate-$CH_3CN$ from 100:0 to 0:100 in 15 min; the flow rate was 0.5 mL/min. Peaks were detected by UV absorption with a diode array detector at 230, 254, and 280 nm. All derivatives tested for biological activity showed >95% purity by HPLC analysis (detection at 254 nm). Low-resolution mass spectrometry was performed with a JEOL SX102 spectrometer with 6 kV Xe atoms following desorption from a glycerol matrix or on an Agilent LC/MS 1100 MSD, with a Waters (Milford, Mass.) Atlantis C18 column. High resolution mass spectroscopic (HRMS) measurements were performed on a proteomics optimized Q-TOF-2 (MicromassWaters) using external calibration with polyalanine, unless noted. Observed mass accuracies are those expected based on known instrument performance as well as trends in masses of standard compounds observed at intervals during the series of measurements. Reported masses are observed masses uncorrected for this time dependent drift in mass accuracy. c Log P and tPSA (total polar surface area) was calculated using ChemDraw Professional (PerkinElmer, Boston, Mass. v. 19.0). Compound 17 was prepared as reported in Chambers et al., J. Biol. Chem. 2000, 275, 10767-10771.

Synthesis Shown in Schemes 1 & 2:

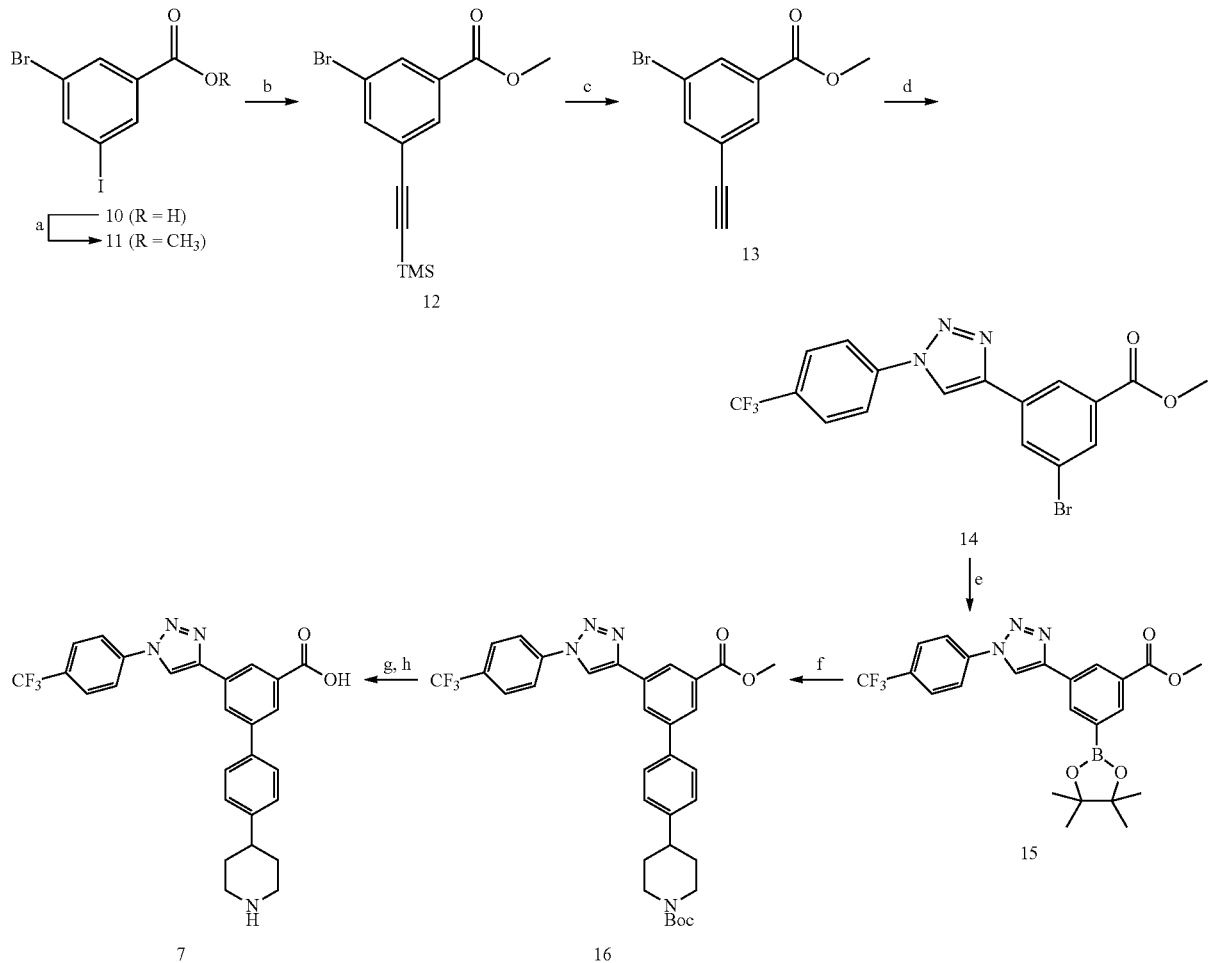

Synthesis of reverse triazole 7.
Reagents and Conditions: (a) SOCl2, MeOH, rt, 15 h, 96%; (b) TMS-acetylene, PdCl2(PPh3)2, CuI, Et3N, DMF, rt, 5 h, 92%; (c) TBAF, THF, rt, 0.5 h, 94%; (d) 1-azido-4-(trifluoromethyl)benzene, CuSO4•5H2O, Na ascorbate, THF:H2O, rt, 1 h, 46%; (e) B2(pin)2, KOAc, PdCl2(dppf), dioxane, 70° C., 15 h, 76%; (f) te-t-butyl 4-(4-bromophenyl)piperidine-1-carboxylate, Pd(PPh)4, K2CO3, DMF, 85° C., 2 h (39%); (g) KOH, MeOH, H2O, 50° C., 15 h, 60-99%; (h) TFA:THF = 1:1, rt, 1 h, 61%.

General Procedure: Deprotection Reaction

Method A: A mixture of compound (1 eq) and potassium hydroxide (5 eq) in methanol:water (2:1) was stirred at 50° C. This mixture was neutralized with 1N HCl until pH was 5-6. The slightly acidic mixture was evaporated under reduced pressure and purified by silica gel column chromatography (dichloromethane:methanol:acetic acid=95:5:0.1) or semipreparative HPLC (10 mM triethylammonium acetate buffer:acetonitrile=80:20 to 20:80 in 40 min) to afford the compound as a white solid.

Method B: A solution of compound in trifluoroacetic acid:tetrahydrofuran (2:1) was stirred at room temperature. The solvent was evaporated with toluene under reduced pressure. The residue was purified by silica gel column chromatography (dichloromethane:methanol=95:5) or semi-preparative HPLC (10 mM triethylammonium acetate buffer:acetonitrile=80:20 to 20:80 in 40 min) to afford the compound as a white solid.

Methyl 3-bromo-5-iodobenzoate (11). To a solution of 3-bromo-5-iodobenzoic acid (10, 500 mg, 1.53 mmol) in methanol (7.5 mL) was added dropwise thionyl chloride (1.1 mL, 2.18 g, 18.35 mmol) at 0° C., and then this reaction mixture was stirred at room temperature for 15 h. After being neutralized with saturated NaHCO$_3$ solution on the ice bath, the mixture was extracted with ethyl acetate (20 mL×2). The combined organic layer was washed with brine, dried over MgSO$_4$, filtered and evaporated under reduced pressure to afford compound 11 (498 mg, 96%) as a white solid; 1H NMR (400 MHz, CDCl$_3$) δ 8.32 (t, J=1.40 Hz, 1H), 8.15 (t, J=1.58 Hz, 1H), 8.06 (t, J=1.64 Hz, 1H), 3.95 (s, 3H); MS (ESI, m/z) 340.9, 342.9 [M+1]$^+$; ESI-HRMS calcd. m/z for $C_8H_7O_2I^{79}Br$ 340.8674, found 340.8672 [M+1]$^+$.

Methyl 3-bromo-5-((trimethylsilyl)ethynyl)benzoate (12). To a solution of compound 11 (100 mg, 0.293 mmol) in N,N-dimethylformamide (2 mL) were added PdCl$_2$(PPh$_3$)$_2$ (41 mg, 0.058 mmol), copper iodide (5 mg, 0.029 mmol), triethylamine (0.122 mL, 178 mg, 1.76 mmol), TMS-acetylene (0.045 mL, 0.322 mmol), and then this reaction mixture was stirred at room temperature for 5 h. After the solvent was evaporated under reduced pressure, the residue was purified by silica gel column chromatography (hexane:ethyl acetate=50:1) to afford compound 12 (84 mg, 92%) as a colorless syrup; 1H NMR (400 MHz, CDCl$_3$) δ 8.12 (t, J=1.70 Hz, 1H), 8.06 (t, J=1.44 Hz, 1H), 7.79 (t, J=1.68 Hz, 1H), 3.94 (s, 3H), 0.27 (s, 9H); MS (ESI, m/z) 311.0, 313.0 [M+1]$^+$; ESI-HRMS calcd. m/z for $C_{13}H_{16}O_2^{79}BrSi$ 311.0103, found 311.0104 [M+1]$^+$.

Methyl 3-bromo-5-ethynylbenzoate (13). To a solution of compound 12 (76 mg, 0.244 mmol) in tetrahydrofuran (2 mL) was added tetrabutylammonium fluoride (0.02 mL, 1 M solution in tetrahydrofuran), and then this reaction mixture was stirred at room temperature for 0.5 h. After being neutralized with acetic acid, the mixture was evaporated under reduced pressure. The residue was purified by silica gel column chromatography (hexane:ethyl acetate=30:1) to afford compound 13 (55 mg, 94%) as a white solid; 1H NMR (400 MHz, CDCl$_3$) δ 8.16 (t, J=1.70 Hz, 1H), 8.10 (t, J=1.44 Hz, 1H), 7.82 (t, J=1.68 Hz, 1H), 3.95 (s, 3H), 3.19 (s, 1H); MS (ESI, m/z) 239.0, 241.0 [M+1]$^+$; ESI-HRMS calcd. m/z for $C_{10}H_8O_2^{79}Br$ 238.9708, found 238.9709 [M+1]$^+$.

Methyl 3-bromo-5-(1-(4-(trifluoromethyl)phenyl)-1H-1,2,3-triazol-4-yl)benzoate (14). To a solution of compound 13 (49 mg, 0.205 mmol) and 1-azido-4-(trifluoromethyl)benzene (60 μL, 0.307 mmol, synthesized according to literature procedures reported) in tetrahydrofuran:water (2 mL, 1:1) were added CuSO$_4$·5H$_2$O (25 mg, 0.102 mmol) and sodium ascorbate (61 mg, 0.307 mmol, freshly prepared 1 M aqueous solution), and then this reaction mixture was stirred at room temperature for 1 h. The reaction mixture was partitioned with diethyl ether (10 mL) and water (5 mL), and the aqueous layer was extracted with diethyl ether (10 mL×2). The combined organic layer was washed with brine (5 mL), dried over MgSO$_4$, filtered and evaporated under reduced pressure. The residue was purified by silica gel column chromatography (hexane:ethyl acetate=9:1) to afford compound 14 (40 mg, 46%) as a white solid; 1H NMR (400 MHz, CDCl$_3$) δ 8.44 (t, J=1.48 Hz, 1H), 8.38 (s, 1H), 8.36 (t, J=1.74 Hz, 1H), 8.18 (t, J=1.64 Hz, 1H), 7.98 (d, J=8.44 Hz, 2H), 7.86 (d, J=8.56 Hz, 2H), 3.98 (s, 3H); MS (ESI, m/z) 426.0, 428.0 [M+1]$^+$; ESI-HRMS calcd. m/z for $C_{17}H_{12}N_3O_2F_3^{79}Br$ 426.0065, found 426.0063 [M+1]$^+$.

Methyl 3-(4,4,5,5-tetramethyl-1,3,2-dioxaborolan-2-yl)-5-(1-(4-(trifluoromethyl)phenyl)-1H-1,2,3-triazol-4-yl)benzoate (15). To a solution of compound 14 (305 mg, 0.716 mmol) in 1,4-dioxane (10 mL) were added bis(pinacolato)diboron (363 mg, 1.43 mmol), PdCl$_2$(dppf) (12 mg, 14.3 μmol) and potassium acetate (210 mg, 2.15 mmol), and then this reaction mixture was stirred at 70° C. for 15 h. The reaction mixture was partitioned with ethyl acetate (20 mL) and water (10 mL), and the aqueous layer was extracted with ethyl acetate (10 mL×2). The combined organic layer was washed with brine (5 mL), dried over MgSO$_4$, filtered and evaporated under reduced pressure. The residue was purified by silica gel column chromatography (hexane:ethyl acetate=2:1) to afford compound 15 (258 mg, 76%) as a white solid; 1H NMR (400 MHz, CDCl$_3$) δ 8.72 (s, 1H), 8.54 (s, 1H), 8.50 (s, 1H), 8.41 (s, 1H), 8.00 (d, J=8.28 Hz, 2H), 7.86 (d, J=8.32 Hz, 2H), 3.99 (s, 3H), 1.41 (s, 12H); MS (ESI, m/z) 474.2 [M+1]$^+$; ESI-HRMS calcd. m/z for $C_{23}H_{24}N_3O_4F_3B$ 474.1812, found 474.1804 [M+1]$^+$.

tert-Butyl 4-(3'-(methoxycarbonyl)-5'-(1-(4-(trifluoromethyl)phenyl)-1H-1,2,3-triazol-4-yl)-[1,1'-biphenyl]-4-yl)piperidine-1-carboxylate (16a). The mixture of compound 15 (26 mg, 0.055 mmol), Pd(PPh$_3$)$_4$ (3.8 mg, 3.29 μmol) and potassium carbonate (23 mg, 0.165 mmol) in N,N-dimethylformamide (1.5 mL) was purged with nitrogen gas for 15 min, and then NBoc-(4-bromophenyl)piperidine (28 mg, 0.082 mmol) was added to the mixture. The mixture was stirred at 85° C. for 2 h, and then allowed to be cooled to room temperature. This mixture was partitioned with diethyl ether (5 mL) and water (10 mL). The aqueous layer was extracted with diethyl ether (5 mL×2), and then the combined organic layer was washed with brine (3 mL), dried over MgSO$_4$, filtered and evaporated under reduced pressure. The residue was purified by silica gel column chromatography (hexane:ethyl acetate=4:1) to afford compound 16a (13 mg, 39%) as a white solid; 1H NMR (400 MHz, CD$_3$OD) δ 9.26 (s, 1H), 8.57 (s, 1H), 8.45 (s, 1H), 8.27 (s, 1H), 8.20 (d, J=8.44 Hz, 2H), 7.95 (d, J=8.56 Hz, 2H), 7.71 (d, J=8.20 Hz, 2H), 7.41 (d, J=8.20 Hz, 2H), 4.26 (d, J=12.96 Hz, 2H), 4.00 (s, 3H), 2.93 (broad s, 2H), 2.86-2.79 (m, 1H), 1.90 (d, J=12.40 Hz, 2H), 1.72-1.61 (m, 2), 1.51 (s, 9H); MS (ESI, m/z) 551.2 [M+1]$^+$; ESI-HRMS calcd. m/z for $C_{29}H_{26}N_4O_4F_3$ 551.1906, found 551.1902 [M+1]$^+$.

4'-(1-(ten-Butoxycarbonyl)piperidin-4-yl)-5-(1-(4-(trifluoromethyl)phenyl)-1H-1,2,3-triazol-4-yl)-[1,1'-biphenyl]-3-carboxylic acid (16b). Method A: Yield 60%; 1H NMR (400 MHz, CD$_3$OD) δ 9.20 (s, 1H), 8.53 (s, 1H), 8.39 (s, 1H), 8.25 (s, 1H), 8.18 (d, J=7.92 Hz, 2H), 7.93 (d, J=8.20 Hz, 2H), 7.68 (d, J=7.76 Hz, 2H), 7.37 (d, J=7.84 Hz, 2H), 4.25 (d, J=13.12 Hz, 2H), 2.91 (broad s, 2H), 2.80 (t, J=12.02 Hz, 1H), 1.88 (d, J=12.68 Hz, 2H), 1.70-1.60 (m, 2H), 1.51 (s, 9H).

4'-(Piperidin-4-yl)-5-(1-(4-(trifluormethyl)phenyl)-1H-1,2,3-triazol-4-yl)-[1,1'-biphenyl]-3-carboxylic acid (7). Method B: Yield 61%; HPLC purity 95% (R$_t$=11.17 min); 1H NMR (400 MHz, CD$_3$OD) δ 9.18 (s, 1H), 8.43 (s, 1H), 8.34 (s, 1H), 8.28 (s, 1H), 8.23 (d, J=8.52 Hz, 2H), 7.96 (d, J=8.56 Hz, 2H), 7.73 (d, J=8.16 Hz, 2H), 7.39 (d, J=8.12 Hz, 2H), 3.19 (d, J=12.28 Hz, 2H), 2.82-2.74 (m, 3H), 2.67 (s, 3H; OAc salt), 1.89 (d, J=8.24 Hz, 2H), 1.80-1.70 (m, 2H); MS (ESI, m/z) 493.2 [M+1]$^+$; ESI-HRMS calcd. m/z for $C_{27}H_{24}N_4O_2F_3$ 493.1851. found 493.1856 [M+1]$^+$.

Scheme 2. Synthesis of N-acyl derivatives of PPTN 1, i.e. Compounds 4 and 5.

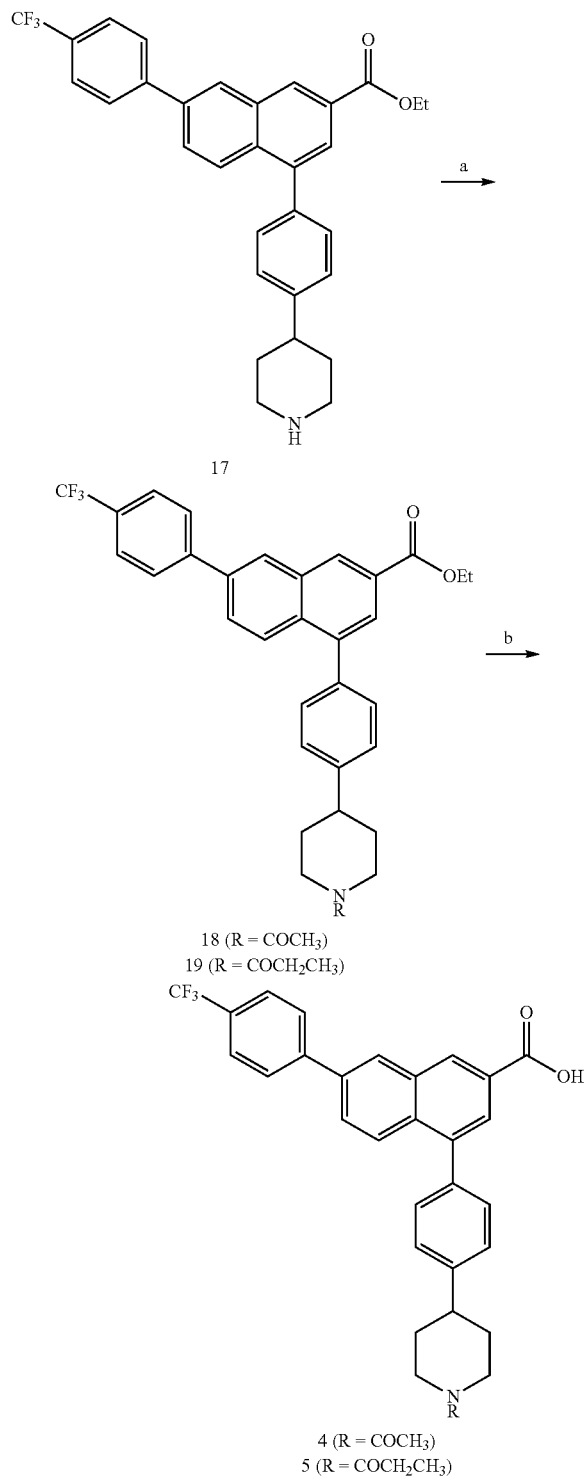

18 (R = COCH₃)
19 (R = COCH₂CH₃)

4 (R = COCH₃)
5 (R = COCH₂CH₃)

Reagents and Conditions: (a) Ac₂O, Et₃N, CH₃CN, rt, 0.5 h, 49% for 4; propionic acid, HATU, DIPEA, DMF, rt, 2 h, 54% for 5; (b) KOH, MeOH, H₂O, 50° C., 67-99% (Method A, above).

Acylation of 17 to Yield 18 and 19:

Ethyl 4-(4-(1-acetylpiperidin-4-yl)phenyl)-7-(4-(trifluoromethyl)phenyl)-2-naphthoate (18). To a solution of compound 17 (30.0 mg, 0.060 mmol) in acetonitrile (2.0 mL) was added triethylamine (12 µl, 0.120 mmol) by dropwise addition at room temperature. After this reaction mixture was stirred for 5 min, acetic anhydride (18 µl, 0.180 mmol) was added to the reaction mixture. Then, this reaction mixture was stirred at room temperature for 30 min. This mixture was partitioned with ethyl acetate (5 mL) and brine (10 mL). The aqueous layer was extracted with ethyl acetate (5 mL×2), and then the combined organic layer was dried with MgSO₄, filtered and evaporated under reduced pressure. The residue was purified by silica gel column chromatography (hexane:ethyl acetate=1:1) to afford 18 (26 mg, 49%) as a white solid; $^1$H NMR (400 MHz, CDCl₃) δ 8.68 (s, 1H), 8.23 (s, 1H), 8.05-8.03 (m, 2H), 7.83-7.74 (m, 5H), 7.49 (d, J=7.96 Hz, 2H), 7.37 (d, J=7.88 Hz, 2H), 4.86-4.83 (m, 1H), 4.47 (q, J=7.08 Hz, 2H), 4.013.98 (m, 1H), 3.27-3.20 (m, 1H), 2.89-2.83 (m, 1H), 2.72-2.66 (m, 1H), 2.17 (s, 3H), 2.04-1.98 (m, 2H), 1.75-1.70 (m, 2H), 1.45 (t, J=7.08 Hz, 3H); MS (ESI, m/z) 546.2 [M+1]⁺; ESI-HRMS calcd. m/z for C₃₃H₃₁NO₃F₃ 546.2256. found 546.2250 [M+1]⁺.

Ethyl 4-(4-(1-propionylpiperidin-4-yl)phenyl)-7-(4-(trifluoromethyl)phenyl)-2-naphthoate (19). To a solution of compounds 17 (33 mg, 0.065 mmol) in N,N-dimethylformamide (2.0 mL) were added propionic acid (5 µL, 0.072 mmol), HATU (27.0 mg, 0.072 mmol) and N,N-diisopropylethylamine (15 µL, 0.085 mmol), and then this reaction mixture was stirred at room temperature for 2 h. The reaction mixture was partitioned with ethyl acetate (5 mL) and water (5 mL), and the aqueous layer was extracted with ethyl acetate (5 mL×2). The combined organic layer was washed with brine (3 mL), dried with MgSO₄, filtered and evaporated under reduced pressure. The residue was purified by silica gel column chromatography (hexane:ethyl acetate=3:1) to afford compound 19 (20 mg, 54%) as a white solid; $^1$H NMR (400 MHz, CD₃OD) δ 8.60 (s, 1H), 8.28 (s, 1H), 7.92-7.87 (m, 4H), 7.79-7.73 (m, 3H), 7.35 (s, 4H), 4.744.70 (m, 1H), 4.42 (q, J=7.12 Hz, 2H), 4.12-4.07 (m, 1H), 3.26-3.19 (m, 1H), 2.94-2.86 (m, 1H), 2.77-2.70 (m, 1H), 2.48 (q, J=7.48 Hz, 2H), 2.02-1.91 (m, 2H), 1.76-1.58 (m, 2H), 1.42 (t, J=7.12 Hz, 3H), 1.16 (t, J=7.48 Hz, 3H); MS (ESI, m/z) 560.2 [M+1]⁺; ESI-HRMS calcd. m/z for C₃₄H₃₃NO₃F₃ 560.2413, found 560.2419 [M+1]⁺.

4-(4-(1-(Acetyl)piperidin-4-yl)phenyl)-7-(4-(trifluoromethyl)phenyl)-2-naphthoic acid (4). Method A: Yield 67%; HPLC purity 99% (R$_t$=9.79 min); $^1$H NMR (400 MHz, CD₃OD) δ 8.71 (s, 1H), 8.38 (s, 1H), 8.00-7.95 (m, 4H), 7.89-7.87 (m, 1H), 7.79 (d, J=8.12 Hz, 2H), 7.47-7.41 (m, 4H), 4.74-4.70 (m, 1H), 4.11-4.06 (m, 1H), 3.27-3.25 (m, 1H), 2.97-2.91 (m, 1H), 2.80-2.73 (m, 1H) 2.16 (s, 3H), 2.04-1.98 (m, 2H), 1.83-1.66 (m, 2H); MS (ESI, m/z) 518.2 [M+1]⁺; ESI-HRMS calcd. m/z for C₃₁H₂₇NO₃F₃ 518.1943, found 518.1949 [M+1]⁺.

4-(4-(1-(Propionyl)piperidin-4-yl)phenyl)-7-(4-(trifluoromethyl)phenyl)-2-naphthoic acid (5). Method A: Yield 79%; HPLC purity 99% (R$_t$=10.29 min); $^1$H NMR (400 MHz, CD₃OD) δ 8.70 (s, 1H), 8.38 (s, 1H), 8.00-7.95 (m, 4H), 7.89-7.87 (m, 1H), 7.79 (d, J=8.08 Hz, 2H), 7.45-7.40 (m, 4H), 4.76-4.71 (m, 1H), 4.14-4.10 (m, 1H), 3.25-3.21 (m, 1H), 2.97-2.91 (m, 1H), 2.79-2.72 (m, 1H), 2.49 (q, J=7.48 Hz, 2H), 2.03-1.96 (m, 2H), 1.77-1.65 (m, 2H), 1.16 (t, J=7.48 Hz, 3H); MS (ESI, m/z) 532.2 [M+1]⁺; ESI-HRMS calcd. m/z for C₃₂H₂₉NO₃F₃ 532.2100, found 532.2102 [M+1]⁺.

In Vitro Pharmacological Methods

Establishment of HEK293 Cell Lines Stably Expressing mP2Y$_{14}$R.

Transfection of human embryonic kidney 293 (HEK293) cells was accomplished using Lipofectamine 2000 (Invitrogen, Carlsbad, Calif.), and selection occurred in the presence of 0.5 mg/mL of G418. A copy of the 1029 bp ORF sequence of the mP2Y$_{14}$R (gene: mouse P2ry14) cloned into pcDNA3.1+N·HA was purchased from GenScript (Project ID U7499CG210-1, GenScript, Piscataway, N.J.). This cloning vector incorporates a human influenza hemagglutinin (HA)-TAG to the N terminus of the expressed protein, and the plasmid contains the selective marker for neomycin resistance.

HEK293 cells were grown in Eagle's minimal essential medium (EMEM) supplemented with 10% fetal bovine serum, penicillin (100 U/mL) and streptomycin (100 µg/mL) at 37° C. in a 5% $CO_2$ environment. Freshly plated overnight cultures were grown to 80% confluency in 6-well plates. Following the manufacturer's transfection protocol, 12 µg of plasmid DNA was suspended in 700 jtL of serum-free Opti-MEM medium (Gibco, Gaithersburg, Md.) by gentle vortex-mixing. Four tubes of diluted Lipofectamine 2000 (15 µL in 150 µL of serum-free Opti-MEM medium, Invitrogen, Carlsbad, Calif.) were prepared. 150 µL of the DNA suspension was added to each diluted lipofectamine tubes and allowed to incubate at room temperature for 5 min. The 250 µL of the DNA-lipid complex was slowly added to four of the wells containing the HEK293 cells and incubated 48 h at 37° C. After 48 h of incubation, cells were detached using Corning CellStripper Dissociation Reagent (Thermo Fisher, Rockville, Md.) and transferred to 150 mm petri dish. The culture medium was replaced with media containing G418 at a concentration of 0.555 mg/mL for the selection of mP2Y$_{14}$R-expressing cells. Selection proceeded until the formation of well isolated single clonal colonies of geneticin resistant cells was established (2-3 weeks). Single clonal colonies were picked via cloning rings, expanded and assayed for cell surface HA-TAG expression by flow cytometry. Fluorescent assays were performed on a BD FACSCalibur flow cytometer (BD Biosciences, San Jose, Calif.) in conjunction with the software packages BD Bioscience PlateManager and CellQuest. Subsequent assay for high mP2Y$_{14}$R expression was conducted on HA-TAG positive cells using the known AlexaFluor488 (AF488)-labeled P2Y$_{14}$R ligand 20 (FIGS. 1A-1D). Cell lines exhibiting high 20 binding, determined by flow cytometry, were used for this Example.

Cell Culture.

HEK293 cells stably expressing mP2Y$_{14}$R (HEK293-mP2Y$_{14}$R) were grown in EMEM supplemented with 10% fetal bovine serum, penicillin (100 units/mL), streptomycin (100 µg/mL), and G418 sulfate (0.555 mg/mL). Cells were maintained in a humidified atmosphere and sterile incubating conditions held at 37° C. and 5% $CO_2$ (g).

Chinese hamster ovary cells stably expressing hP2Y$_{14}$R (CHO-hP2Y$_{14}$R) were grown in Dulbecco's Modified Eagle Medium/Ham's F12 (DMEM/F12) 1:1 supplemented with 10% fetal bovine serum, penicillin (100 units/mL), streptomycin (100 µg/mL), and G418 sulfate (0.500 mg/mL). Cells were maintained in a humidified atmosphere and sterile incubating conditions held at 37° C. and 5% $CO_2$(g).

Fluorescence Microscopy of HEK293-mP2Y14R. HEK293-mP2Y14R cells were grown in an p-slide 8 well coverslip (Ibidi, Martinsried, Germany) coated with laminin and used when 70-80% confluency was reached. Incubation of cells with a fixed concentration of 20 (200 nM) for 45 min was performed following 45 min of incubation in the absence or presence of antagonist PPTN 1 (1 µM) at 37° C. and 5% $CO_2$ (g). At the end of the incubation, cells were washed with sterile 1× Dulbecco's Phosphate-Buffered Saline (DBPS) plus $Ca^{2+}/Mg^{2+}$ and then incubated with 2 µg/mL of Hoechst 33342 solution for 15 min. After three consecutive washes in DPBS ($+Ca^{2+}/Mg^{2+}$), 200 µL of FluoroBrite DMEM was added to each well and cells were visualized using a Keyence BZ-9000 Fluorescence Microscope equipped with a GFP band pass filter set. The objective lens used was Nikon PlanApo 20×/0.75.

Competitive Binding Assay of P2Y14R. All Competitive fluorescent assays were performed on a BD FACSCalibur flow cytometer in conjunction with the software BD Bioscience PlateManager and CellQuest. Assay of antagonist binding to the hP2Y14R expressed in CHO cells using flat-bottom 96-well plates was performed as described in Yu et al., *J. Med. Chem.* 2018, 61, 4860-4882. For binding assay at the mouse homologue, HEK293-mP2Y14R cells were grown in a 24-well plate and used when 80-90% confluency was reached. Unlabeled ligands are stored as 5 mM stock solutions in dimethyl sulfoxide (DMSO). A serial dilution of each compound was prepared in EMEM supplemented with 10% fetal bovine serum, penicillin (100 units/mL), streptomycin (100 µg/mL), and G418 sulfate (0.555 mg/mL) to generate solutions with different concentration of unlabeled antagonist range from 100 µM-1 nM. Cells were initially incubated with unlabeled antagonists (prepared as described) for 30 min at 37° C. and 5% $CO_2$ (g). Cells were then incubated with 20 for 30 min at a final concentration of 20 nM. At the end of the incubation, cells were washed three times with 500 µL sterile 1×DPBS minus $Ca^{2+}/Mg^{2+}$. HEK293-mP2Y14R cells were then detached from the plate using Corning Cellstripper. Cells were resuspended in sterile 1×DPBS minus $Ca^{2+}/Mg^{2+}$ and transferred to a 96-well plate for flow cytometry.

$IC_{50}$ values were determined from the gathered data using Prism 8.0 (GraphPad, San Diego, Calif.).

In Vivo Pharmacological Methods

Animals:

Adult male ICR mice (20-30 g) were purchased from Envigo (Indianapolis, Ind.). Animals were kept under 12-hour light/dark cycle with food and water available ad libitum and regulated temperature (20-22° C.) and humidity (55-65%).

Chronic Constriction Injury:

Chronic constriction injury (CCI) to the sciatic nerve was performed using the Bennett model. In brief, the mice were anesthetized using 2-2.5% isoflurane/oxygen and the hair on the left hind limb was shaved. Then the animals were placed on a sterile surgical field and the skin was wiped with topical antiseptic, Dermachlor solution (0.2% chlorhexidine gluconate). A continuous 2-2.5% isoflurane/oxygen was maintained throughout the procedure. A small incision was created on the lateral side of the left hind limb parallel to the femur. The sciatic nerve was exposed and ligated on two sites about 1 mm apart above the trifurcation using silk sutures 6.0. The incision was closed with clips and lidocaine cream was applied.

Test Compounds:

The antagonists were initially dissolved in 100% DMSO (with 1 equivalent of 1 N NaOH added to dissolve compound (4) and systemically administered in the mice (0.2 mL, i.p.) 7 days after CCI, using 30% DMSO in sterile saline as vehicle.

Behavioral Testing of Mechano-Allodynia:

Mice were acclimated to the testing mesh-rack for 30 min before behavioral measurements. All behavioral testing was performed in the morning. The baseline measurements were determined on day 0 before CCI procedure. On day 7 post-CCI, baseline behavior responses were assessed, beginning prior to drug administration. Following drug injection, the behaviors were evaluated at multiple time points. Mechano-allodynia was quantified according to the hind paw withdrawal response to von Frey filaments stimulation by the Dixon up-and-down method. Briefly, testing was performed by placing the tip of the filament perpendicular to the plantar surface of the hind paw for 2-5 s, until the filament buckled. A series of 8 von Frey filaments (0.04, 0.07, 0.16, 0.4, 0.6, 1.0, 1.4 and 2.0 g; Stoelting, Wood Dale, Ill.) were used. In presence of a positive withdrawal response a lighter filament was applied. If a negative response occurred, a stronger filament was used. At least four readings are obtained after the first positive response and the pattern of response was converted to a 50% paw withdrawal threshold (PWT), using the method described by Chaplan et al., *J. Neurosci. Methods* 1994, 53(1), 55-63.

Statistical Analysis:

Data are expressed as mean±SD and analyzed by two-tailed, two-way repeated measures ANOVA with Dunnett's post hoc comparisons to day 7 behavior. The percentage of reversal of peak CCI-induced pain afforded by each drug was calculated for each animal using their baseline and day 7 post CCI behavioral measures. % Reversal=(PWT(g)$_t$−PWT(g)$_{day7}$)/PWT(g)$_{day0}$−PWT(g)$_{day7}$)×100, where PWT (g)=paw withdrawal threshold, t=time after drug. The ED50 (dosed that caused reversal of mechano-allodynia by 50% at time of peak reversal, 1 h post drug delivery) values were calculated by least squares nonlinear regression of $\log_{10}$ of the compound concentration versus the normalized response (% reversal at 1 h) with an assumed Hill slope=1. All statistical analyses were performed using GraphPad Prism 8 (Graph Pad Inc., San Diego, Calif.). Significance was accepted at p<0.05.

Results and Discussion

The P2Y$_{14}$R antagonists used in this Example include both reference compounds previously reported (1-3, 6, 8) and newly synthesized analogues (4, 5 and 7). The analogues tested included potent reference antagonist 1, its truncated 2 and N-hexynyl 3 derivatives, N-acyl derivatives 4 and 5, and derivatives with a phenyl-triazole moiety replacing the naphthalene ring system in 6-8. The novel antagonists 4, 5 and 7 were synthesized (Schemes 1 & 2), and their P2Y$_{14}$R affinities were comparable to the other members of the series. The mP2Y$_{14}$R and hP2Y$_{14}$R affinities were either similar or differed by up to 2-4 fold, in either direction (Table 1). The elongated chains of 3 and 8 moderately reduced, but did not preclude, receptor binding affinity, which was consistent with the placement of the phenylpiperidine moiety in 1 or its replacement thiophene in 8 pointing toward the hP2Y$_{14}$R exofacial side.

TABLE 1

P2Y$_{14}$R binding affinities in a whole cell assay and predicted physical properties of the antagonists in two species.

| Compound | cLogP[a] | tPSA (Å$^2$)[a] | Mouse (nM)[b] | Human (nM)[b] |
|---|---|---|---|---|
| 1 | 5.65 | 49.3 | 21.6 ± 7.0 | 6.0 ± 0.1 |
| 2 | 5.50 | 57.5 | 1600 ± 250 | 3200 ± 640 |
| 3 | 7.21 | 40.5 | 130 ± 30 | 76.3 ± 24.4 |
| 4 | 6.97 | 45.6 | 29.7 ± 9.3 | 27.6 ± 4.3 |
| 5 | 7.49 | 57.6 | 38.0[c] | 41.8 ± 1.8 |
| 6 | 4.23 | 77.3 | 142 ± 58 | 31.7 ± 8.0 |
| 7 | 4.23 | 77.3 | 246 ± 63 | 664 ± 175 |
| 8 | 3.00 | 120.4 | 384 ± 88 | 169 ± 42 |

[a]Calculated partition coefficient (cLogP) and total polar surface area (tPSA) calculated using ChemDraw 19.0.
[b]Affinity determined as an IC50 using a fluorescent antagonist tracer 20 by flow cytometry detection in mammalian cells expressing the receptor (hP2Y$_{14}$R in CHO cells; mP2Y$_{14}$R in HEK293 cells). N = 3-4, unless noted.
[c]N = 1.
ND, not determined.

Compound 7 contains a triazole ring that is reversed in orientation compared to reported antagonists 6 and 8. Synthesis of 7 was performed using a Sonogashira reaction (11 to 12), click reaction (13 to 14) and a Suzuki reaction (15 to 16) followed by two-step deprotection. Reversed triazole 7, compared to its isomer 6, had 21-fold lower affinity at hP2Y$_{14}$R, but was nearly equipotent at mP2Y$_{14}$R. N-Acetylation of 1 to form 4 maintained its mP2Y$_{14}$R affinity, while the hP2Y$_{14}$R affinity was 4-fold reduced. The lack of potent off-target activity of novel analogues 4 and 7 at 45 different receptors and channels (Table 2, Ki values at several biogenic amine receptors>1 µM) also justified their use as P2Y$_{14}$R probes. Compound 1 and several congeners were inactive at other P2YRs. The potential agonist/antagonist activity of 1 was also determined at the CB$_1$ and CB$_2$ cannabinoid receptors using a PRESTO-Tango assay; IC$_{50}$ values were >50 µM and EC$_{50}$ determinations showed no evidence of activation (see FIGS. 2A-2D).

TABLE 2

Compound, PDSP number: Ki (nM, ± SEM)

1, PPTN, 37482: DOR, 2750; D$_3$, 6790.
2, MRS4519, not tested.
3, MRS4149, 52188: σ$_1$, 465; σ$_2$, 159.
4, MRS4625, 55252: 5HT$_{1D}$, 1750 ± 540; 5HT$_{1E}$, 3910 ± 350; 5HT$_{5A}$, 2340 ± 1250; D$_1$, 1390 ± 120; α$_{1A}$, 3140 ± 680; α$_{2C}$, 4310 ± 820; β$_3$, 860 ± 400; TSPO, 508 ± 44.
5, MRS4626, not tested.
6, MRS4217, 37481: none.
7, MRS4525, 50325: α$_{2A}$, 959; α$_{2B}$, 5326; α$_{2C}$, 2710 ± 210; DOR, 3790; σ$_1$, 1480; σ$_2$, 2090.
8, MRS4458, 45181: DOR, 5300; 5HT$_{1D}$, 6700.

P2Y$_{14}$R antagonists were screened first at a dose of 10 µmol/kg i.p. to examine if they are effective in reversing neuropathic pain resulting from peripheral nerve injury. Using chronic constriction injury of the sciatic nerve in mouse at day 7 (time required to achieve peak pain), the antagonists reversed the chronic mechano-allodynia to varying degrees and duration starting from 30 min and most lasting at least 3 h (FIGS. 3A-3D & 5A-5F). No difference in paw withdrawal threshold (PWT) was observed for any of the P2Y$_{14}$R antagonists versus vehicle control at the contralateral hind paw. Time of peak protection was 1 h for most compounds, but 1-2 h for 4. Two compounds (1 and 4) completely reversed mechano-allodynia (100% at—1 h, Table 2), and other analogues were less efficacious. Compound 4 showed the greatest in vivo efficacy at 5 h, with 40.7±7.5% protection (P<0.05 vs. day 7). The duration of action could be estimated by the ratio of protection at 3 h divided by the protection at 5 h. This ratio was high (0.72-0.92) for 1, 4 and 5, medium (0.34-0.63) for 2, 7 and 8, and low (0.13) for 3. Thus, P2Y$_{14}$R antagonists rapidly (<30 min) reversed mechano-allodynia, with maximal effects typically within 1 h after injection.

The in vivo efficacy of the two potent isomeric triazole derivatives 6 and 7 were compared at 10 μmol/kg i.p., but there was no statistical difference between their in vivo effects. Lower doses of three compounds, parent naphthalene 1, its N-acetyl derivative 4 and triazole reference compound 6 (1 and 3 μmol/kg i.p., Table 3), were examined in order to determine their potency. The ED$_{50}$ values at 1 h in units of μmol/kg (95% CI) were: 1, 1.6 (0.79-2.9); 4, 2.0 (1.1-3.8); 6, 3.5 (1.8-7.0), with no statistical differences observed.

TABLE 3

Reversal of chronic neuropathic pain in the mouse CCI model, expressed as percent inhibition of mechano-allodynia on day 7 (n = 3).

| Compound | Dose, μmol/kg, i.p. | Effect at 0.5 h (% ± SD) | Effect at 1 h (% + SD) | Effect at 2 h (% ± SD) | Effect at 3 h (% ± SD) | Effect at 5 h (% ± SD) |
|---|---|---|---|---|---|---|
| 1 | 1 | 10.0 ± 17.3 | 19.9 ± 17.3 | 10.0 ± 17.3 | 4.7 ± 8.2 | 4.7 ± 8.2 |
|   | 3 | 62.9 ± 18.7 | 79.3 ± 2.2 | 76.9 ± 6.3 | 64.7 ± 17.2 | 8.7 ± 15.1 |
|   | 10 | 87.9 ± 12.9 | 100 ± 0.0 | 96.4 ± 6.2 | 78.6 ± 9.4 | 21.3 ± 14.1 |
| 2 | 10 | 23.4 ± 21.2 | 64.2 ± 24.9 | 59.8 ± 18.1 | 35.2 ± 22.2 | 0.0 ± 0.0 |
| 3 | 10 | 52.4 ± 23.3 | 75.9 ± 15.0 | 42.7 ± 9.6 | 9.6 ± 16.7 | 0.0 ± 0.0 |
| 4 | 1 | 10.6 ± 18.3 | 14.7 ± 16.0 | 14.7 ± 16.0 | 9.2 ± 8.1 | 10.6 ± 18.3 |
|   | 3 | 37.2 ± 14.5 | 66.3 ± 11.7 | 57.2 ± 7.9 | 37.2 ± 14.5 | 17.0 ± 8.6 |
|   | 10 | 83.3 ± 9.6 | 100 ± 0.0 | 100 ± 0.0 | 92.4 ± 8.7 | 40.7 ± 7.5 |
| 5 | 10 | 32.9 ± 5.7 | 77.2 ± 26.1 | 71.6 ± 19.8 | 55.7 ± 27.1 | 5.6 ± 6.4 |
| 6 | 1 | 8.7 ± 15.1 | 18.7 ± 21.3 | 18.7 ± 21.3 | 8.7 ± 7.6 | 8.7 ± 15.1 |
|   | 3 | 44.6 ± 16.6 | 53.3 ± 24.2 | 44.6 ± 16.6 | 35.6 ± 11.7 | 0.0 ± 0.0 |
|   | 10 | 52.4 ± 9.6 | 67.4 ± 7.0 | 57.2 ± 13.3 | 31.9 ± 16.8 | 12.7 ± 13.2 |
| 7 | 10 | 70.7 ± 16.5 | 86.8 ± 2.4 | 71.4 ± 10.2 | 55.1 ± 18.6 | 6.7 ± 5.9 |
| 8 | 10 | 81.0 ± 6.9 | 91.5 ± 7.4 | 74.0 ± 28.5 | 30.9 ± 21.0 | 10.0 ± 17.3 |

The in vivo efficacy of the compounds did not purely reflect the mP2Y$_{14}$R binding affinity. Therefore, pharmacokinetic factors might influence these activities. Nevertheless, the most potently binding at mP2Y$_{14}$R among the analogues, i.e., 1 and 4 (IC$_{50}$ 21.6 and 29.7 nM, respectively), were fully efficacious. The lack of activity of 1 at any other P2YR, its relatively clean off-target profile, and the activities of the other analogues with diverse structural functionalization, including N-acetyl (and alkyl amine 8 (IC$_{50}$ 384 nM at mP2Y$_{14}$R) congeners, supported the conclusion that the in vivo pain protection resulted from blocking the P2Y$_{14}$R. Antagonist 8 of intermediate in vitro affinity and high in vivo efficacy (E$_{max}$ 91.5%) displayed the most favorable c Log P value (3.0) among the analogues. A truncated antagonist >(IC$_{50}$ 1600 nM at mP2Y$_{14}$R) displayed relatively weak in vivo activity, consistent with its lower binding affinity.

Based on physicochemical properties, it is highly unlikely that these compounds readily cross the blood brain barrier. Accordingly, without being bound to theory, it is believed that these antagonists are exerting their effects peripherally by acting on immune cells that infiltrate the DRG or by attenuating activation of DRG-resident cells. It is well established that inhibition of neuronal hyperactivity in the DRG in response to immune cell/resident cells activation in the DRG profoundly alters spinal cord signaling. Thus, blocking peripheral sensitization will attenuate central sensitization.

It is shown in this Example, that P2Y$_{14}$R antagonists are effective, in a dose-dependent manner, in reversing neuropathic pain resulting from peripheral nerve injury. This is the first demonstration that P2Y$_{14}$R antagonists reverse chronic neuropathic pain in the mouse CCI model. This model has been predictive of compounds that eventually became approved treatment for chronic neuropathic pain.

In order to correlate the in vivo activity with receptor affinity, a previous fluorescent binding assay in whole cells to the mP2Y$_{14}$R, which was found adequately expressed in an HEK293 stable cell line, was modified to analyze protection against mechano-allodynia by already reported P2Y$_{14}$R antagonists, including the widely-used antagonist 1 (ED$_{50}$ 1.6 μmol/kg i.p.), with several novel derivatives: simple N-acyl derivatives of 1, i.e., 4 and 5, and a reversed triazole derivative 7 related to reported antagonist 6. The in vivo efficacy of 7 was similar to its parent triazole 6. N-Acetyl derivative 4, with significant protection even after 5 h, was equi-efficacious in vivo, to its parent piperidine derivative 1. Thus, antagonizing the P2Y$_{14}$R is now established as a target for chronic neuropathic pain treatment.

Example 2

In this Example, a P2Y14R antagonist was analyzed in a mouse model of chronic neuropathic pain (sciatic constriction).

Figure 5:
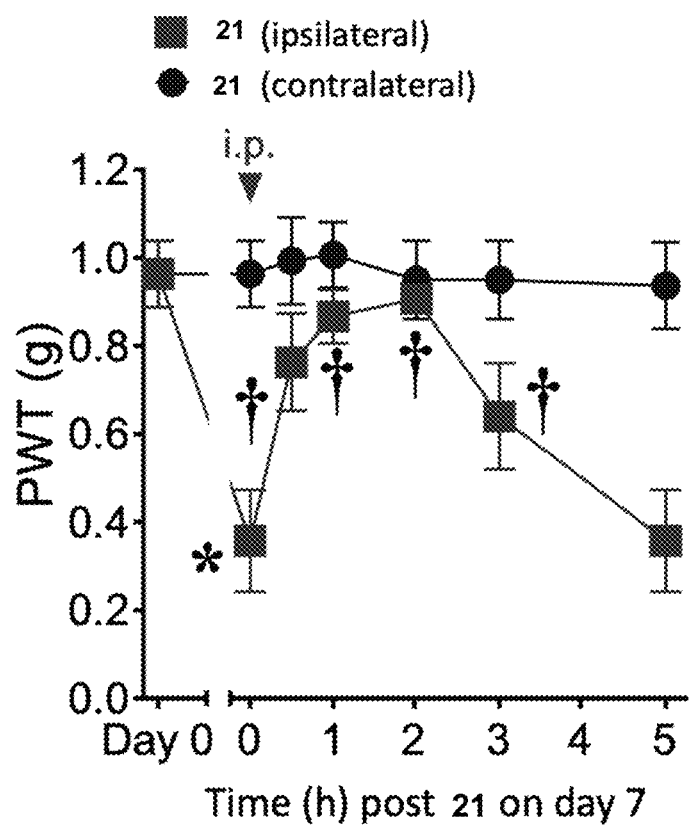
FIG. 5 depicts in vivo efficacy of MRS4571; 21, in a mouse model of unilateral chronic neuropathic pain. The dose was 10 µmol/kg, i.p., injected in a volume of 0.2 mL in a vehicle of 30% DMSO in phosphate-buffered saline. Mechano-allodynia in the ipsilateral and contralateral hind paws was measured manually using von Frey filaments. Data (Mean±SD) were analyzed by two-way ANOVA, *P<0.05 versus day 0 and †P<0.05 versus day 7, n=3.

The PEG conjugate, MRS4571 (compound 21) displayed ~20-fold greater aqueous solubility at pH 7.4 than compound 1. So, its in vivo efficacy was measured in a mouse model of chronic neuropathic pain (7 days post-chronic constriction injury, CCI, of the sciatic nerve in adult male mice) using the methods of Example 1. As shown in FIG. 5, compound 21 was fully efficacious in reversing established, CCI-induced mechano-allodynia at a dose that was shown to be effective for other more potent P2Y14R antagonists such as 1 and 8 (10 μmol/kg, i.p.) as analyzed in Example 1. Peak protection was achieved at 1-2 h post injection. No effect of the drug was seen on the hind paw response contralateral to the injury.

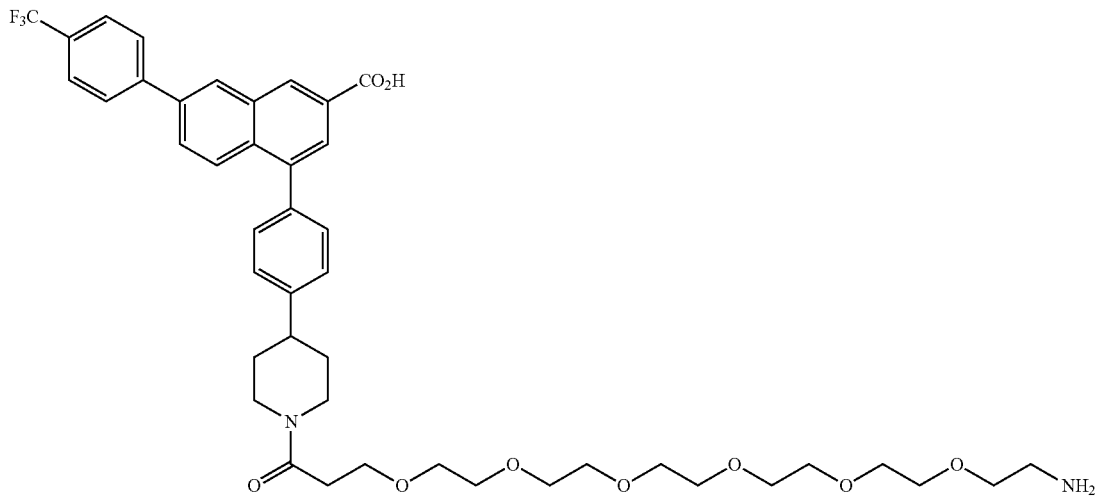

(21)

In view of the above, it will be seen that the several advantages of the disclosure are achieved and other advantageous results attained. As various changes could be made in the above methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A method for treating neuropathic pain in a subject in need thereof, the method comprising: administering to the subject in need thereof a therapeutically effective amount of an antagonist of P2Y14 of formula (III)

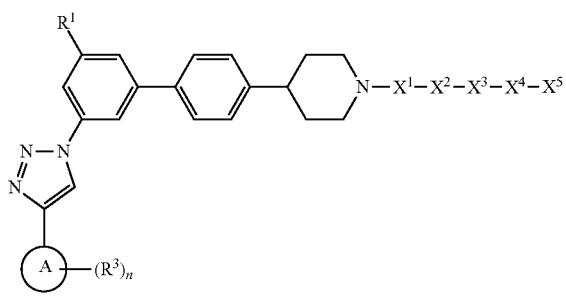

(III)

or a pharmaceutically acceptable salt thereof, wherein ring A is aryl, heteroaryl, or cycloalkyl; $R^1$ is —$CO_2H$, —$CO_2$($C_1$-$C_8$ alkyl), or a bioisostere of carboxylate; each $R^3$ is independently $C_1$-$C_8$ alkyl, $C_2$-$C_8$ alkenyl, $C_3$-$C_6$cycloalkyl, hydroxy, hydroxyalkyl, $C_1$-$C_8$ alkoxy, $C_3$-$C_6$cycloalkyloxy, aryloxy, halo, $C_1$-$C_8$ haloalkyl, $C_1$-$C_8$ haloalkoxy, —CN, —$NO_2$, —$NR^5R^6$, —C(O)$R^4$, —$CO_2R^4$, —C(O)$NR^5R^6$, —$NR^5$C(O)$R^4$, —($CH_2$)$_m$aryl, —($CH_2$)$_m$heteroaryl, or —($CH_2$)$_m$heterocycloalkyl; $R^4$, $R^5$, and $R^6$ are independently H or $C_1$-$C_8$ alkyl; $X^1$ is selected from the group consisting of —($CH_2$)$_o$—, —C(O)—, —C(O)NH—, —OC(O)NH—, —OC(O)—, —C(O)O—, —C(S)NH—, and —$SO_2$—; $X^2$ is selected from the group consisting of

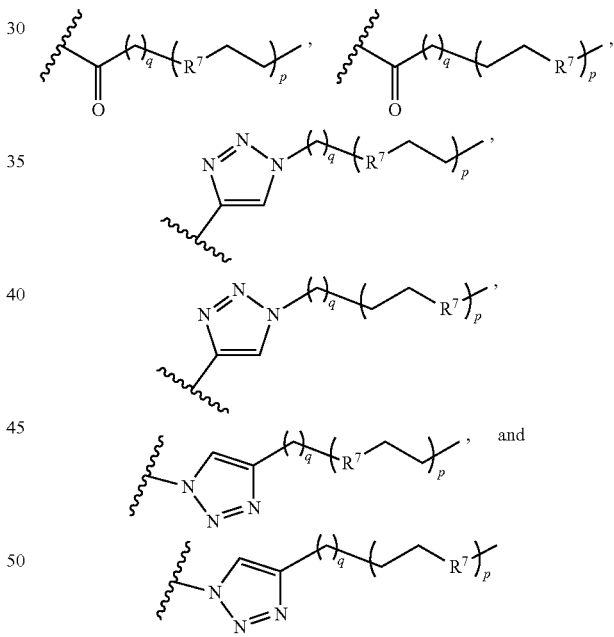

wherein $R^7$ is $CH_2$, NH, or O; $X^3$ is a dendron; $X^4$ is selected from the group consisting of —($CH_2$)o-, —C(O)—, —C(O)NH—, —OC(O)NH—, —OC(O)—, —C(O)O—, —C(S)NH—, —$SO_2$—, —NHC(O)—, and $X^5$ is a reactive sulfur-containing moiety; m, n, and q are independently 0 or an integer from 1-5; o is an integer from 1-5; and p is 0 or an integer from 1-36.

2. The method of claim 1, wherein in formula (III), the dendron is carboxyethylpolyamido (CEPAM) dendron that is optionally functionalized in at least one position to include the moiety

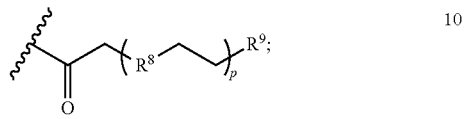

wherein $R^8$ is $CH_2$, NH, or O, and $R^9$ is —$NH_2$ or —$CO_2H$.

* * * * *